United States Patent [19]
Jirkovsky et al.

[11] 3,995,052
[45] Nov. 30, 1976

[54] INDENOPYRAN- AND INDENOTHIOPYRANALKYLAMINES III IN THE TREATMENT OF DEPRESSION

[75] Inventors: Ivo Jirkovsky, Montreal; Leslie G. Humber, Dollard des Ormeaux; Christopher A. Demerson, Montreal; Thomas A. Dobson, Dollard des Ormeaux, all of Canada

[73] Assignee: Ayerst McKenna and Harrison Ltd., Montreal, Canada

[22] Filed: May 19, 1975

[21] Appl. No.: 578,688

Related U.S. Application Data

[63] Continuation-in-part of Ser. No. 377,696, July 9, 1973, which is a continuation-in-part of Ser. No. 297,129, Oct. 12, 1972, Pat. No. 3,778,449.

[52] U.S. Cl. ............................... 424/275; 424/248; 424/250; 424/267; 424/274; 424/283
[51] Int. Cl.² .................. A61K 31/35; A61K 31/38; A61K 31/40; A61K 31/445; A61K 31/495; A61K 31/535

[58] Field of Search .......... 424/248, 250, 267, 274, 424/275, 283

*Primary Examiner*—Stanley J. Friedman

[57] ABSTRACT

Indenopyran- and indenothiopyranalkylamine derivatives characterized by having an amino(lower)alkyl radical attached to the 1 position of an indeno[2,1-c]pyran or indeno[2,1-c]thiopyran nucleus are disclosed. Also included are the corresponding derivatives having an indeno[1,2-c]pyran and an indeno[1,2-c]-thiopyran nucleus. The amino portion of the amino(lower)alkyl radical may be further substituted with one or two lower alkyl groups or incoporated into a heterocyclic amine radical. The derivatives are further substituted at position 1 and may be optionally substituted at positions 3, 4, 5, 6, 7, 8, and 9. The indenopyran- and indenothiopyranalkylamine derivatives of this invention are useful antidepressant agents. Methods for their preparation and use are disclosed.

32 Claims, No Drawings

INDENOPYRAN- AND INDENOTHIOPYRANALKYLAMINES III IN THE TREATMENT OF DEPRESSION

This Application is a Continuation-in-Part of our earlier-filed application Ser. No. 377,696, filed July 9, 1973, which is a Continuation-in-Part of our earlier-filed application Ser. No. 297,129, filed Oct. 12, 1972 (now U.S. Pat. No. 3,778,449, issued Dec. 11, 1973).

BACKGROUND OF THE INVENTION

1. Field of Invention

This invention relates to novel indenopyran- and indenothiopyranalkylamine derivatives, to processes for their preparation and to intermediates used in these processes.

More specifically, the present invention relates to novel indenopyran- and indenothiopyranalkylamine derivatives possessing valuable pharmacologic properties. For example, these derivatives exhibit useful antidepressant properties at dosages which do no elicit undesirable side effects. The combination of this property together with a low order of toxicity render the indenopyran- and indenothiopyranalkylamines of the invention therapeutically useful.

2. Description of the Prior Art

Prior interest in the field of indenopyrans and indenothiopyrans has been so limited that it may be considered practically non-existant. Apparently, the closest prior art to the compounds of the present invention would be a few unrelated reports dealing with chemical aspects of certain compounds with indenopyran ring systems. For example, in a report by N. Campbell, et al., J. Chem. Soc., 993 (1963), the authors postulate that certain neutral indeno[2,1-c]or indeno[1,2-c]pyran derivatives may be produced by the reaction of 2-benzylideneindan-1-one and diphenylketene.

SUMMARY OF THE INVENTION

The indenopyran- and indenothiopyranalkylamine derivatives of this invention are characterized by having an amino(lower)alkyl radical attached to a indenopyran or indenothiopyran nucleus. The preferred derivatives of this invention are represented by formulae 1 or 1a,

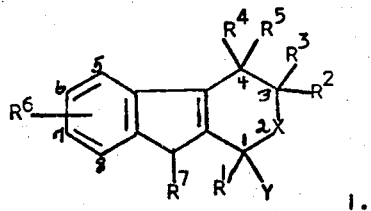

I.

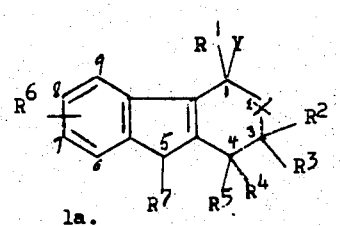

1a.

in which $R^1$ is lower alkyl; $R^2$, $R^3$, $R^4$ and $R^5$ are the same or different selected from the group consisting of hydrogen and lower alkyl; $R^6$ is hydrogen, lower alkyl, hydroxy, lower alkoxy, lower alkanoyloxy or halo; $R^7$ is hydrogen or lower alkyl; X is oxy or thio; and Y is an amino (lower)alkyl radical of formula —Alk—$NR^8R^9$ wherein Alk is an alkylene selected from the group consisting of $CR^{10}R^{11}$, $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ wherein $R^{10}$, $R^{11}$, $R^{12}$, $R^{13}$, $R^{14}$, $R^{15}$, $R^{16}$ and $R^{17}$ are hydrogen or lower alkyl and $R^8$ and $R^9$ are either the same or different selected from the group consisting of hydrogen and lower alkyl, or $R^8$ and $R^9$ together with the nitrogen atom to which they are joined form a heterocyclic amine radical selected from the group consisting of 1-pyrrolidinyl, piperidino, morpholino, piperazino, 4-(lower alkyl)-1-piperazinyl and 4-[hydroxy(lower)-alkyl]-1-piperazinyl.

DETAILED DESCRIPTION OF THE INVENTION

The term "lower alkyl" as used herein contemplates straight chain alkyl radicals containing from one to six carbon atoms and branched chain alkyl radicals containing three to four carbon atoms and includes methyl, ethyl propyl, isopropyl, butyl, isobutyl, pentyl and the like.

The term "lower alkoxy" as used herein contemplates both straight and branched chain alkoxy radicals containing from one to four carbon atoms and includes methoxy, ethoxy, isopropoxy and the like.

The term "lower alkanoyloxy" as used herein contemplates both straight and branched chain alkanoyloxy radicals containing from two to six carbon atoms and includes acetoxy, propionyloxy, hexanoyloxy and the like.

The term "halo" as used herein contemplates halogens and includes fluorine, chlorine, bromine and iodine.

The indenopyran- and indenothiopyranalkylamines of formulae I and Ia are capable of forming acid addition salts with pharmaceutically acceptable acids. Such acid addition salts are included within the scope of this invention.

The acid addition salts are prepared by reacting the base form of the appropriate indenopyran- and indenothiopyranalkylamines with substantially one or two equivalents, depending on the number of basic nitrogens in the compound, or preferably with an excess of the appropriate acid in an organic solvent, for example, ether or an ethanol-ether mixture. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

Also included in this invention are the stereochemical isomers of the compounds of formulae 1 and 1a which result from asymmetric centers, contained therein. These isomeric forms may be prepared by chemical methods and are purified readily by crystallization or chromatography.

Individual optical isomers, which might be separated by fractional crystallization of the diastereoisomeric salts formed thereof, for instance, with d- or l-tartaric acid or D-(+)-α-bromocamphor sulfonic acid, are also included.

Antidepressant Activity

The useful antidepressant activity of the indenopyran- and indenothiopyranalkylamines of formulae I and Ia and their acid addition salts with pharmaceutically acceptable acids may be demonstrated in standard pharmacologic tests, such as, for example, the tests described by F. Hafliger and V. Burckhart in "Psychopharmacological Agents", M. Gordon, Ed., Academic Press, New York and London, 1964, pp. 75–83.

More specifically, as noted in the latter reference the antidepressant properties of a compound may be demonstrated by its capacity to antagonize the depressant effects of reserpine. Furthermore, it is well documented that reserpine in animals produces a model depression which can be used for detecting antidepressant properties. Accordingly, the compounds of the present invention antagonize reserpine effects in mice at doses ranging from about 1 to 100 mg/kg. Several of the preferred compounds, for instance, N,N,1-trimethyl-1,3,4,9-tetrahydroindeno[2,1-c]pyran-1-ethylamine hydrochloride (Example 284),
N,N,1-trimethyl-1,3,4,9-tetrahydroindeno[2,1-c]pyran-1-propylamine hydrochloride (Example 287),
N,N,1-trimethyl-1,3,4,9-tetrahydroindeno[2,1-c]thiopyran-1-ethylamine hydrochloride (Example 373), and N,N,1-trimethyl-1,3,4,5-tetrahydroindeno[1,2-c]pyran-1-ethylamine hydrochloride (Example 480) antagonize the effects of reserpine in mice at dose ranges from about 1 to 15 mk/kg.

The compounds of the present invention are also particularly noteworthy in that they block substantially the uptake of seratonin. This property, which is readily demonstrated in the test of D. F. Bogdanski et al., J. Pharmac. Exp. Ther., 122, 182 (1958), is a desirable feature for a therapeutic agent used to alleviate the symptoms of depression especially when it is desired primarily to elevate the mood of the patient.

When the indenopyran- and indenothiopyranalkylamines of this invention are used to relieve the symptoms of depression in warm-blooded mammals, e.g. rats and mice, they may be used alone or in combination with pharmacologically acceptable carriers, the proportion of which is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects and preferably at a level that is in a range of from about 0.1 mg to about 50 mg per kilo per day, although as aforementioned variations will occur. However, a dosage level that is in the range of from about 0.5 mg to about 25 mg per kilo per day is most desirably employed in order to achieve effective results.

PROCESSES

For the preparation of the indenopyran- and indenothiopyranalkylamine derivatives of formula I we prefer to use as starting materials the compounds of general formula II,

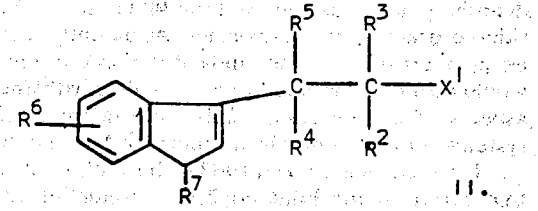

in which $R^2$, $R^3$, $R^4$, $R^5$, $R^6$ and $R^7$ are as defined in the first instance and $X^1$ is hydroxy, mercapto, —S—SO$_3$—Na or —S—SO$_3$K.

The starting material of formula II, indene-3-ethanol (II; $X^1$ = OH and $R^2$, $R^3$, $R^4$, $R^5$, $R^6$ and $R^7$ = H), is well known and its synthesis by a variety of methods has been reported; for example, see G. R. Clemo, et al., J. Chem Soc., 863 (1951), and F. H. Howell and D. A. H. Taylor, J. Chem. Soc., 3011 (1957). For the preparation of this starting material as well as the other requisite starting materials of formula II in which $X^1$ is hydroxy the following two general processes are convenient.

The first process may be illustrated as follows:

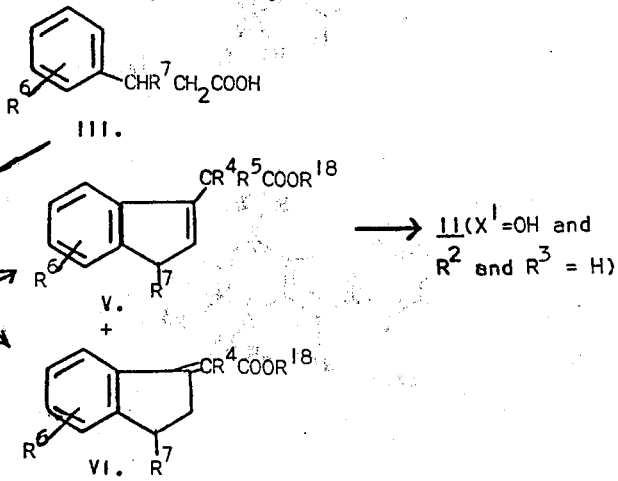

With reference to this first process the cyclization of the appropriate phenylpropionic acid derivative, see "Chemistry of Carbon Compounds", Vol. III A, E. H. Rodd, Ed., Elsevier Publishing Co., Amsterdam, 1954, pp. 593–598, is accomplished by treatment with an acid, for example, anhydrous hydrofluoric acid, according to the conditions described by J. A. Elvidge and R. G. Foster, J. Chem. Soc., 590 (1963), to give the corresponding indanone of formula IV. The latter compound is treated with the appropriate Reformatski reagent of formula $ZCR^4R^5COOR^{18}$ in which Z is bromine or chlorine, $R^{18}$ is lower alkyl and $R^4$ and $R^5$ are as defined hereinbefore, followed by dehydration of the product, see "Organic Reactions", Vol. I, R. Adams, et al., Eds., John Wiley and Sons, Inc., New York, 1942, p. 1 and K. Brewster, et al., J. Chem. Soc., 941 (1972), to give the "endo" ester V or a mixture thereof with the "exo" ester VI in the case where $R^5$ of the Reformatski reagent is hydrogen. The ester V or the mixture of the latter esters are then reduced by lithium aluminum hydride and the desired compound of formula II ($X^1 =$ OH and $R^2$ and $R^3 =$ H) separated from the reaction product by conventional means such as chromatography or recrystallization.

The second process may be illustrated as follows:

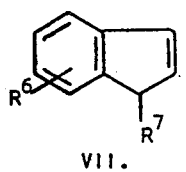

VII.

+

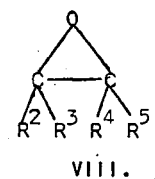

VIII.

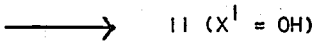

II ($X^1 =$ OH)

With reference to this second process the appropriate indene derivative of formula VII, see "Chemistry of the Carbon Compounds", Vol. III B, cited above, 1956, pp. 1256–1261, A. Panetta and S. C. Bunce, J. Org. Chem., 4859 (1961) and M. L. Tamayo and N. D. Robles, Anales Real Soc. Espan. Fis. Y. Quim., 52B, 117 (1956), [Chem. Abst., 50, 14676 (1956)], is converted to its corresponding lithium derivative by treatment with butyl lithium in tetrahydrofuran. The corresponding lithium derivative is then treated with ethylene oxide or a lower alkyl substituted ethylene oxide to afford the desired starting material of formula II in which $X^1$ is hydroxy. The desired starting materials may also be obtained by treating the appropriate ethylene derivative of formula VII with the appropriate ethylene oxide derivative according to the procedure of M. Julia, et al., Bull. Soc. Chim. Fr., 2291 (1966), for reacting ethylene oxide with indole.

The lower alkyl substituted ethylene oxides are prepared by known methods; for example, see V. Franzen and H. E. Driesen, Chem. Ber., 96 881 (1963).

The starting materials of formula II in which $X^1$ is mercapto, $-S-SO_3-Na$ or $-S-SO_3-K$ and $R^2$, $R^3$, $R^4$, $R^5$, $R^6$ and $R^7$ are as defined in the first instance may be obtained by the following process: The appropriate compound of formula II ($X^1 =$ OH), described above, is treated with phosphorus tribromide in an inert solvent, for example, ether or carbon tetrachloride, to afford the corresponding 3-(2-bromoethyl)indene derivative. In the case where $X^1$ is hydroxy and $R^2$, $R^3$, $R^4$, $R^5$, $R^6$ and $R^7$ are hydrogen, the corresponding 3-(2-bromoethyl)indene derivative obtained is 3-(2-bromoethyl)indene itself, also described by R. Clemo, et al., J. Chem. Soc., 863 (1951). The 3-(2-bromoethyl)indene derivative so obtained is then converted to the desired starting material of formula II ($X^1 =$ SH, $S-SO_3-Na$ or $S-SO_3-K$) by a procedure similar to that described by N. N. Suvorov and V. N. Buyanov, Khim.-Farm. Zh., I, (1967), [Chem. Abstr. 67, 73474a (1967)], for converting 3-(2-bromoethyl)-indole to indole-3-ethanethiol.

Accordingly, the appropriate 3-(2-bromoethyl)indene derivative is treated with sodium or potassium thiosulfate to afford the corresponding sodium or potassium β-(3-indenyl)ethyl thiosulfate derivative, respectively, namely, the desired starting material of formula II ($X^1 =$ $S-SO_3-Na$ or $S-SO_3-K$). Treatment of the latter derivative with strong alkali, for example, sodium or potassium hydroxide, yields the corresponding bis-[ω-(3-indenyl)ethyl]disulfide derivative. Reduction of the latter compound with lithium aluminum hydride gives the desired compound of formula II in which $X^1$ is mercapto.

On the other hand, the preceding thiosulfate derivative is treated with acid, for example, dilute aqueous solutions of hydrochloric acid, sulfuric acid or phosphoric acid, to give directly the compound of formula II in which $X^1$ is mercapto.

It should be noted that the preceding process may not be entirely practical for the preparation of the compound of formula II in which $X^1$ is mercapto, $-S-SO_3-Na$ or $-S-SO_3-K$ and $R^6$ is hydroxy or lower alkanoyloxy. For this reason, the preferred starting materials of formula II for the ultimate preparation of the compounds of formula I in which $R^6$ is hydroxy or lower alkanoyloxy and X is thio, $-S-SO_3-Na$ or $-S-SO_3K$ are the corresponding compounds of formula II in which $R^6$ is benzyloxy, i.e., a hydroxyl with a protecting benzyl group or other suitable protecting group, see J. F. McOmie, "Advances in Organic Chemistry", Vol. 3, R. A. Raphael, et al, Ed., Interscience Publishers, New York, 1963, pp. 191–294. When the latter compounds are used as starting materials in this manner, they are first subjected to the process (II + IX → X), described below. Subsequently, the benzyloxy group is removed by hydrogenation, in the presence of a catalyst, for example, 10% palladium on carbon, just prior to affording the desired corresponding compound of formula I in which $R^6$ is hydroxy. The latter may be converted if desired to the corresponding compound of formula I in which $R^6$ is lower alkanoyloxy by conventional means, for example, by treatment with the appropriate lower alkanoic anhydride preferably in the presence of pyridine.

Likewise, it should be noted that similar use of the starting materials of formula II in which $X^1$ is hydroxy and $R^6$ is benzyloxy to obtain the corresponding compound of formula I in which $R^6$ is hydroxy or lower alkanoyloxy is also preferred.

The above described starting material of formula II in which $R^2$, $R^3$, $R^4$, $R^5$, $R^6$, $R^7$ and $X^1$ are as defined in the first instance is utilized for the preparation of the corresponding compound of formula I by subjecting it to a key reaction comprising the treatment of said starting material with substantially an equivalent amount of a compound of formula

 (IX)

in which $R^1$ is as defined in the first instance and $Y^1$ is selected from the group consisting of:

a. $COOR^{19}$ and $Alk^1-COOR^{19}$ in which $R^{19}$ is hydrogen or lower alkyl and $Alk^1$ is an alkylene selected from the group consisting of $CR^{10}R^{11}$, $CR^{10}R^{11}CR^{12}R^{13}$ and $CR^{10}R^{11}CR^{12}R^{13}CR^{14}R^{15}$ wherein $R^{10}$, $R^{11}$, $R^{12}$, $R^{13}$, $R^{14}$ and $R^{15}$ are hydrogen or lower alkyl, b. $CONR^8R^9$ and $Alk^1-CONR^8R^9$ in which $Alk^1$, $R^8$ and $R^9$ are as defined hereinbefore, c. $CH_2OCOR^{20}$ and $Alk^1-CH_2OCOR^{20}$ in which $R^{20}$ is hydrogen or lower alkyl and $Alk^1$ is as defined hereinbefore, d. $Alk^2-L$ in which $Alk^2$ is an alkylene selected from the group consisting of $CR^{10}R^{11}CHR^{12}$, $CR^{10}R^{11}CR^{12}R^{13}CHR^{14}$ and $CR^{10}R^{11}CR^{12}R^{13}CR^{14}R^{15}CHR^{16}$ wherein $R^{10}$, $R^{11}$, $R^{12}$, $R^{13}$, $R^{14}$, $R^{15}$, and $R^{16}$ are as defined hereinbefore and L is halo, e. $Alk\ NR^{20}COR^{21}$ in which Alk and $R^{20}$ are as defined herein and $R^{21}$ is hydrogen or lower alkyl containing from one to five carbon atoms, f. $Alk-NO_2$ in which Alk is as defined hereinbefore, and g. $AlkNR^8R^9$ in which Alk, $R^8$ and $R^9$ are as defined hereinbefore, in the presence of an acid catalyst to yield the compound of formula X in which $R^1$, $R^2$, $R^3$, $R^4$, $R^5$, $R^6$, $R^7$, X and $Y^1$ are as defined hereinbefore,

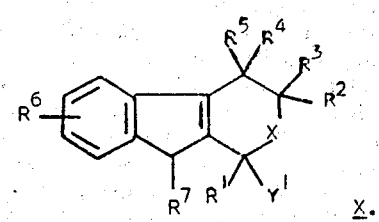

followed, when said compound of formula X is different from said compound of formula I, by transformation of said compound of formula X into a compound of formula I by the application of standard methods known to be effective for said transformation for other compounds.

Accordingly, when $Y^1$ is the group $Alk-NR^8R^9$, the compound of formula I is obtained directly, and when $Y^1$ is other than $Alk-NR^8R^9$, as noted above, the novel compounds of formula I are prepared by transformation of said compounds of formula X by standard methods, several of the more convenient and practical methods being described in detail hereinafter.

When practising the condensation (II + IX → X) a solvent is generally used as a reaction medium. Any solvent inert to the reaction conditions may be used. Suitable solvents include benzene, toluene, diethyl ether, dioxan, tetrahydrofuran, methylene dichloride, carbon tetrachloride and the like. Benzene and tetrahydrofuran are especially convenient and practical for this use. However, note that the solvent may be omitted without detrimental effects on the reaction if the reactants are heated to a melt with stirring.

A variety of suitable acid catalysts may be used for this condensation, for example, the type of catalyst used in a Friedel-Crafts reaction, i.e., p-toluenesulfonic acid, aluminum chloride, phosphorus pentoxide, boron trifluoride, zinc chloride, hydrochloric acid, perchloric acid, trifluoroacetic acid, sulfuric acid, and polyphosphoric acid and the like. Boron trifluoride, p-toluenesulfonic acid, aluminum chloride, and trifluoroacetic acid are included amoung the preferred acid catalysts. The amount of acid catalyst used is not especially critical and may range from 0.01 molar equivalents to 100 molar equivalents with respect to the starting material of formula II. A range of from 0.1 to 10 molar equivalents is generally preferred; however, note that the amount of acid catalyst should be in excess of one molar equivalent with respect to the compound of formula

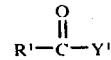

when $Y^1$ is $AlkNR^8R^9$.

The time of the reaction may range from 10 minutes to 60 hours, with the preferred range being from ½ to 24 hours. The temperature of the reaction may range from 20° to 160° C.

A more detailed description of the preparation of the above compounds of formula X and a description of their subsequent conversion and indenopyran- and indenothiopyranalkylamine derivatives of formula I are disclosed below. For convenience these descriptions are catagorized into sections according to the group selected for $Y^1$ for the intermediate.

a. Preparation and Conversion of Intermediates of Formula X ($Y^1 = COOR^{19}$ and $Alk^1-COOR^{19}$)

Intermediates of formula X ($Y^1 = COOR^{19}$ and $Alk^1-COOR^{19}$ wherein $R^{19}$ is hydrogen or lower alkyl and $Alk^1$ is as defined in the first instance) are readily obtained by the condensation (II + IX → X) by using ketoacids or ketoesters of formula

in which $R^1$ is as defined in the first instance and $Y^1$ is $COOR^{19}$ or $Alk^1-COOR^{19}$ as defined above together with the starting material of formula II.

Generally comparable yields of product are obtained in this process when either the ketoacid or the corresponding ketoester is used. However, in the case where it is desired to prepare an acid compound of formula X in which $Y^1$ is $Alk^1COOR^{19}$ wherein $Alk^1$ is $CR^{10}R^{11}$ and $R^{19}$ is hydrogen (i.e., an acid intermediate of formula X), it is preferable to first condense the appropriate β-ketoester of formula IX rather than the corresponding β-ketoacid and then hydrolyze the resulting ester product to give the desired acid compound.

Moreover, in the general practise of this invention it is often more convenient to prepare the acid compounds of formula X by using the ketoester instead of the ketoacid in this process and hydrolyze the resulting ester product to the desired acid, the reason being simply that the ketoesters are generally more readily available either commercially or by synthesis.

The hydrolysis of compounds of formula X in which $Y^1$ is $COOR^{19}$ or $Alk^1COOR^{19}$ wherein $Alk^1$ is as defined in the first instance and $R^{19}$ is lower alkyl, i.e. ester intermediates of formula X, to their corresponding acids of formula X, is readily effected by treatment with a suitable alkali, for example, potassium hydroxide or sodium carbonate, in aqueous methanol or aqueous ethanol or by treatment with lithium iodide in a suitable organic solvent, for example, collidine, see L. F. Fieser and M. Fieser, "Reagents for Organic Synthesis", John Wiley and Sons, Inc., New York, 1967, pp. 615–617.

The α-, β-, γ- and δ-ketoacids and -ketoesters of formula IX are either known, for example, ethyl pyruvate, levulinic acid, ethyl α,α-dimethylacetoacetate, and β,β-dimethyllevulic acid, or they may be prepared by known methods described in general organic chemistry textbooks. For example, a comprehensive review of the properties and preparation of such α-, β-, γ- and δ-ketoacids and ketoesters may be found in "Rodd's Chemistry of the Carbon Compounds", S. Coffey, Ed., Vol. Id, 2nd ed., Elsevier Publishing Co., Amsterdam, 1965, pp. 226–274.

Thereafter these intermediate acids and esters of formula X are converted by amidation followed by reduction to compounds of formula I in which $R^1$, $R^2$, $R^3$, $R^4$, $R^5$, $R^6$, $R^7$ and X are as defined in the first instance and Y is $-Alk-NR^8R^9$ in which Alk is $CH_2$ or $Alk^{1'}CH_2$ wherein $Alk^1$ is as defined in the first instance.

More specifically, in the case where the acid intermediate of formula X is employed, said acid is subjected to amidation by treatment with a lower alkyl chloroformate, preferably ethyl chloroformate, in the presence of triethylamine, affording the corresponding mixed anhydride, which is converted by treatment with the appropriate amine of formula $HNR^8R^9$ in which $R^8$ and $R^9$ are as defined in the first instance, for example, ammonia, methylamine and dimethylamine, to yield the corresponding amide of formula X in which $Y^1$ is $CONR^8R^9$ or $Alk^1CONR^8R^9$ in which $Alk^1$, $R^8$ and $R^9$ are as described in the first instance.

Alternatively, the latter amides are also obtained by treating the ester intermediates of formula IX with the appropriate amine according to known amidation methods, for example, See A. L. F. Beckwith in "The Chemistry of Amides", J. Zalicky, Ed., Interscience Publishers, New York, 1970, pp. 96–105.

Thereafter, the amides so obtained are reduced with a suitable complex metal hydride to yield the desired indenopyran- and indenothiopyranalkylamines. Examples of suitable complex metal hydrides are lithium aluminum hydride, lithium aluminum hydride-aluminum chloride, aluminum hydride-aluminum chloride, diborane and sodium borohydride-aluminum chloride. Lithium aluminum hydride is preferred.

A modification relating to the preceding general reduction of the above amides of formula X in which $Y^1$ is $CONR^8R^9$ or $Alk^1-CONR^8R^9$ wherein $Alk^1$, $R^8$ and $R^9$ is as defined in the first instance is applicable to the reduction of the tertiary, secondary and primary amides, described herein, and is a preferred modification for the reduction of the latter two. In practising this modification, the aforementioned amide of formula X is treated with triethyloxonium fluoroborate or dimethyl sulfate, see H. Bredereck, et al., Chem. Br., 98, 2754 (1965), in an inert solvent, for example, methylene dichloride, whereby the corresponding iminoether fluoroborate or methyl sulfate salt is obtained, respectively. Subsequent reduction of the salt thus obtained with a complex metal hydride, similar to the reduction described previously for the amides, yields the corresponding compounds of formula I. Alternatively, the above fluoroborate or methyl sulfate salt derived from a secondary or primary amide may be decomposed by base treatment, for example, with 10% sodium hydride or triethylamine, to give the corresponding iminoether which is then reduced in a like manner to the desired compound of formula I.

When applying the aforementioned steps in the preparation of compounds of formula I in which $R^6$ is hydroxy or lower alkanoyloxy, it is preferable to use corresponding intermediates in which $R^6$ is benzyloxy followed by the appropriate transformations as noted previously to yield the desired compounds of formula I.

b. Preparation and Conversion of Intermediates of Formula X ($Y^1 = CONR^8R^9$ and $Alk^1-CONR^8R^9$)

The intermediates of formula X in which $Y^1$ is $CONR^8R^9$ and $Alk^1-CONR^8R^9$ wherein $R^8$, $R^9$ and $Alk^1$ are as defined in the first instance, described in the previous section, are also obtained directly by utilizing the appropriate starting materials of formula II and α-, β-, γ- or δ-ketoamides of formula

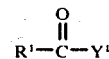

$$R^1-\overset{O}{\underset{\|}{C}}-Y^1$$

in which $R^1$ is as defined above and $Y^1$ is $CONR^8R^9$ or $Alk^1-CONR^8R^9$ in which $Alk^1$, $R^8$ and $R^9$ as as defined above. The ketoamides required for this condensation are either known, for example, pyruvamide or α,α-dimethylacetoacetamide, or they may be prepared by known methods, for instance, see "Rodd's Chemistry of the Carbon Compounds", cited above, Vol. Id, pp. 226–274.

Thereafter these amides are converted by the reduction process, described above, to the compounds of formula I in which $R^1$, $R^2$, $R^3$, $R^4$, $R^5$, $R^6$, $R^7$ and X are as defined in the first instance and Y is $-Alk-NR^8R^9$ in which Alk is $CH_2$ or $Alk^1-CH_2$ wherein $Alk^1$ is as defined in the first instance and $R^8$ and $R^9$ are as defined in the first instance.

c. Preparation and Conversion of Intermediates of Formula X ($Y^1 = CH_2OCOR^{20}$ and $Alk^1—CH_2OCOR^{20}$)

Intermediates of formula X in which $Y^1$ is $CH_2OCOR^{20}$ and $Alk^1—CH_2OCOR^{20}$ wherein $Alk^1$ and $R^{20}$ are as defined in the first instance, are obtained when a starting material of formula II is condensed with a ketoalcohol lower alkanoic acid ester of formula $R^1COCH_2OCOR^{20}$ or $R^1CO—Alk^1—CH_2OCOR^{20}$ in which $R^1$, $Alk^1$ and $R^{20}$ are as defined in the first instance in the presence of a suitable acid catalyst according to the conditions described above for the condensation (II + IX → X). The ketoalcohol lower alkyl esters are either known, for example, acetonyl acetate or 5-acetoxypentan-2-one, or may be prepared by known methods, for instance, see "Rodd's Chemistry of the Carbon Compounds", cited above, Vol. Id, pp. 49–54.

These intermediates of formula X are utilized for the preparation of compounds of formula I of this invention in the following manner: The intermediate is hydrolyzed with an aqueous alcoholic solution of a suitable alkali, for example, sodium hydroxide in aqueous methanol to afford the corresponding primary alcohol. It should be noted also that the latter primary alcohol is obtained directly by the reduction of the appropriate intermediate acids or intermediate esters of formula X, described herein in section (a), using a suitable complex metal hydride as described therein. The primary alcohol is then oxidized to the corresponding aldehyde. Although a variety of methods are known for the oxidation of a primary alcohol to its corresponding aldehyde, see for example, "Rodd's Chemistry of the Carbon Compounds", cited above, Vol. Ic, pp. 4–10, we have found the method of K. E. Pfitzner and J. G. Moffat, J. Am. Chem. Soc., 87, 5670 (1965), using N,N-dicyclohexylcarbodiimide and dimethyl sulfoxide in the presence of a suitable acid, for example, trifluoroacetic acid, to be both efficacious and convenient. Thereafter the aldehyde is reacted with an amine of the formula $HNR^8R^9$ in which $R^8$ and $R^9$ are as defined in the first instance according to the method of K. N. Campbell, et al., J. Amer. Chem. Soc., 70 3868 (1948), in the case when the amine used is ammonia or a primary amine, or according to the method of N. J. Leonard and J. V. Paukstelis, J. Org. Chem., 28, 1937 (1963), when the amine is a secondary amine, to give the corresponding Schiff base or immonium salt, respectively. The product so obtained is reduced with sodium borohydride, see E. Schenker, Angew. Chem., 73, 81 (1961), to yield compounds of formula I in which $R^1$, $R^2$, $R^3$, $R^4$, $R^5$, $R^6$, $R^7$ and X are as defined in the first instance and Y is $—Alk—NR^8R^9$ in which Alk is $CH_2$ or $Alk^1—CH_2$ and $R^8$ and $R^9$ are as defined in the first instance.

Alternatively, the latter compounds of formula I are obtained by converting the above corresponding alcohol to a reactive intermediate such as the corresponding halide, mesylate or tosylate, which is then reacted with two or more molar equivalents of an amine of formula $HNR^8 R^9$ in which $R^8$ and $R^9$ are as defined in the first instance. Preferably this reaction is performed in a suitable inert solvent, for example, tetrahydrofuran, at the boiling point of the reaction mixture for a period of eight to 24 hours. In connection with alkylations of amines of formula $HNR^8R^9$ in which $R^8$ is hydrogen and $R^9$ is lower alkyl as disclosed herein, it is generally preferable to perform the alkylation with the corresponding N-benzyl derivative of said amine, i.e., an amine of formula $HNR^8R^9$ in which $R^8$ is benzyl and $R^9$ is lower alkyl. Thereafter, when all appropriate transformation have been performed, the N-benzyl group may be removed by hydrogenolysis with a catalyst, preferably 10% palladium on carbon, to give the desired compounds of formula I.

Alternatively, the above aldehyde is oxidized with a suitable oxidizing agent to yield the corresponding acid intermediates of formula X described in section (a). Although a variety of suitable oxidizing agents may be used for this purpose, for example, silver oxide, alkaline permanganate, hydrogen peroxide, we prefer to use silver oxide according to the method of M. Delepine and P. Bonnet, Compt. rend., 149, 39 (1909).

Again alternatively, the above aldehyde is converted to its oxime which on reduction with a complex metal hydride yields the corresponding primary amine of formula I in which $R^1$, $R^2$, $R^3$, $R^4$, $R^5$, $R^6$, $R^7$ and X are as defined in the first instance and Y is $—Alk—NR^8R^9$ in which Alk is $CH_2$ or $Alk^1—CH_2$ wherein $Alk^1$ is as defined in the first instance and $R^8$ and $R^9$ are hydrogen.

If desired the latter compounds of formula I may be further N-alkylated on the nitrogen of the primary amine with the appropriate lower alkyl halide to the corresponding compounds of formula I in which Y is $—Alk—NR^8R^9$ wherein Alk is $CH_2$ or $Alk^1—CH_2$ wherein $Alk^1$ is as defined in the first instance and $R^8$ is hydrogen or lower alkyl and $R^9$ is lower alkyl (i.e. secondary or tertiary amines with respect to Y). In this case depending on the particular derivative desired the N-alkylation may be effected with one or two moles of the alkyl halide to give respectively the secondary ($R^8 = H$ and $R^9 = $ lower alkyl) or tertiary amine ($R^8 = R^9 = $ lower alkyl). On the other hand the N-alkylation may be effected in two steps introducing a different alkyl group each time to afford the corresponding tertiary amine in which $R^8$ and $R^9$ are different lower alkyls.

When it is desired to prepare the above tertiary amine compounds in which $R^8$ or $R^9$ are either or both methyl, an alternative alkylation method comprises reacting the appropriate corresponding primary or secondary amine with an aqueous mixture of a substantial excess of formaldehyde and formic acid according to the conditions of the Eschweiler-Clarke reaction, see M. L. Moore, Organic Reactions, 5, 301 (1949), whereby N-methylation is effected.

Another N-alkylation method which may be applied to the above primary and secondary amines involves acylation with a lower alkanoic anhydride or acid halide and subsequent reduction of the resulting amide.

Furthermore, the above primary amines may be used to prepare compounds of formula I in which Y is $—Alk—NR^8R^9$ wherein Alk is $CH_2$ or $Alk^1—CH_2$ and $R^8$ and $R^9$ together with the nitrogen atom to which they are joined from a heterocyclic amine radical as defined in the first instance. When used in this manner the primary amines are subjected to known N-alkylation methods, for example, see method J described by R. B. Moffet, J. Org. Chem., 14, 862 (1949), with the appropriate α,ω-dibromides, for example, tetramethylene dibromide, pentamethylene dibromide, bis(2-chloroethyl)ether, bis(2-chloroethyl)benzylamine followed by hydrogenation in the presence of 10% palladium on carbon to remove the protecting benzyl group, a bis(2-chloroethyl)-lower alkylamine or a bis(2-chloroethyl-N-[hydroxy(lower)-alkyl]amine, to give the corresponding desired compound of formula I wherein Y is an amino(lower)alkyl in which the amino portion thereof is 1-pyrrolidinyl, piperidino, morpholino, piperazino, 4-(lower alkyl)-1-piperazinyl or 4-[hydroxy-(lower)alkyl]-1-piperazinyl, respectively.

d. Preparation and Conversion of Intermediates of Formula X ($Y^1 = Alk^2-L$)

Intermediates of formula X in which $Y^1$ is $Alk^2-L$ wherein $Alk^2$ and L are as defined in the first instance, are obtained when a starting material of formula II is condensed with a β-,γ- or δ-haloketone of formula $R^1CO-Alk^2-L$ in which $R^1$, $Alk^2$ and L are as defined in the first instance, in the presence of a suitable acid catalyst according to the conditions described above for the condensation (II + IX → X).

The haloketones are either known, for example, 4-chlorobutan-2-one, or they may be prepared by known methods, for instance, see "Rodd's Chemistry of Carbon Compounds", cited above, Vol. Ic, pp. 70–71 and "Methoden der Organischen Chemie", Houben-Weyl, E. Müller, Ed., Vol. V/3, Georg Thieme Verlag, Stuttgart, 1962, pp. 511–1076.

Thereafter these intermediates of formula X are treated with two molar equivalents or more of an amine of formula $HNR^8R^9$ in which $R^8$ and $R^9$ are as defined in the first instance to yield the compounds of formula I in which $R^1$, $R^2$, $R^3$, $R^4$, $R^5$, $R^6$, $R^7$ and X are as described in the first instance and Y is $-Alk-NR^8R^9$ in which Alk is $Alk^2$ as defined in the first instance and $R^8$ and $R^9$ are as defined in the first instance. Preferred conditions for this reaction include the use of a suitable inert solvent, for example, tetrahydrofuran, temperatures ranging from 40°–100° C. or at the boiling point of the reaction mixture and a reaction time of from 8 to 24 hours.

e. Preparation and Conversion of Intermediates of Formula X ($Y^1 = AlkNR^{20}COR^{21}$)

Intermediates of formula X in which $Y^1$ is $AlkNR^{20}COR^{21}$ wherein Alk, $R^{20}$ and $R^{21}$ are as defined in the first instance are readily obtained by the condensation (II + IX → X) by using ketoamides of formula

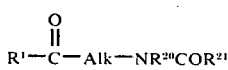

in which $R^1$, Alk, $R^{20}$ and $R^{21}$ are as defined in the first instance together with the appropriate starting material of formula II.

The ketoamides used herein are either known, for example, formamidoacetone [see A. Treibs and W. Sutter, Chem. Ber., 84, 96 (1951) and R. H. Wiley and O. H. Borum, J. Amer. Chem. Soc., 70, 2005 (1948)] or may be prepared by known procedures, for example, see "Methoden der Organischen Chemie", cited above, Vol. XI/1, 1957, especially pp. 58–62, 285–289 and 508–509, and F. F. Blicke, Organic Reactions, I, 303 (1942).

Thereafter, reduction with a complex metal hydride, described in section (a), converts the instant intermediates of formula IX to compounds of formula I in which $R^1$, $R^2$, $R^3$, $R^4$, $R^5$, $R^6$, $R^7$, X are as defined in the first instance and Y is $AlkNR^8R^9$ in which Alk and $R^8$ is hydrogen or lower alkyl and $R^9$ is lower alkyl.

f. Preparation and Conversion of Intermediates of Formula X ($Y^1 = Alk - NO_2$)

Intermediates of formula IX in which $Y^1$ is $Alk-NO_2$ wherein Alk is as defined in the first instance, are obtained by the condensation (II + IX → X) when the starting materials of formula II and appropriate α-, β-, γ- and δ-nitroketones of formula

in which $R^1$ and Alk are as defined in the first instance are employed therein in the presence of a suitable acid catalyst. In this case trifluoroacetic acid is a preferred acid catalyst.

The nitroketones used herein are either known, for example, 1-nitro-2-propanone, N. Levy and C. W. Scaife, J. Chem. Soc., 1100, (1946) and 5-nitro-2-hexanone, J. Shecter, et al., J. Amer. Chem. Soc., 74, 3664 (1952) or they may be prepared by known methods, for example, see Levy and Scaife, cited above, Shechter, et al. cited above, "Rodd's Chemistry of Carbon Compounds", cited above, Vol. Ic, pp. 71–72 and "Methoden der Organischen Chemie", cited above, Vol. X/I, 1971, p. 203.

Thereafter, these intermediates of formula X are reduced with a complex metal hydride, preferably lithium aluminum hydride, to afford the compounds of formula I in which $R^1$, $R^2$, $R^3$, $R^4$, $R^5$, $R^6$, $R^7$ and X are as defined in in the first instance and Z is $-Alk-NR^8R^9$ in which Alk is as defined in the first instance and $R^8$ and $R^9$ are hydrogen.

If desired the latter compounds are N-alkylated according to the methods described in section (c) to give the compounds of formula I in which $R^1$, $R^2$, $R^3$, $R^4$, $R^5$, $R^6$, $R^7$ and X are as defined in the first instance and Y is $Alk-NR^8R^9$ in which Alk is as defined in the first instance, $R^8$ is hydrogen or lower alkyl and $R^9$ is lower alkyl.

g. Preparation of Compounds of Formula X ($Y^1 = AlkNR^8R^9$) ≡ Compound of Formula I (Y = $AlkNR^8R^9$)

The above described starting materials of formula II in which $R^2$, $R^3$, $R^4$, $R^5$, $R^6$, $R^7$ and $X^1$ are as defined in the first instance are condensed in the presence of an acid catalyst with an aminoketone of formula $R^1CO-Alk-NR^8R^9$ in which $R^1$, Alk, $R^8$ and $R^9$ are as defined in the first instance to give directly the indenopyran- and indenothiopyranalkylamine derivatives of formula I of this invention.

The requisite aminoketones for this reaction are either known, for example, 1-dimethylamino-3-butanone, 1-methylamino-3-pentanone, see F. F. Blicke, cited above, or they may be prepared by known procedures, for example, see "Methoden der Organic Chemie", cited above, Vol. XI/I, 1957, pp. 58–62, 285–289 and 508–509.

In practising this present condensation it is generally advantageous to utilize substantially equimolar amounts of the starting material of formula II or IIa and the aminoketone in the presence of an acid catalyst. In this particular condensation the amount of the aforementioned acid catalyst to employ ranges generally from about 1.01 to 100 molar equivalents with respect to the amount of aminoketone reactant, a range of from 1.05 to 10 molar equivalents being preferred. Optionally, one may employ the acid addition salts of the aforementioned aminoketones, for example the hydrochloride or the sulfate salt. In this case the amount of acid catalyst may range from 0.01 to 100 molar equivalents, preferably 0.1 to 10 molar equivalents. Boron trifluoride is a preferred acid catalyst for the present condensation. The reaction may be performed conveniently and advantageously without a solvent, although a high boiling solvent, for example, toluene, o-xylene or isobutyl ether, may be used. Reaction time and temperature depends on the particular reactants employed and may be varied. The most convenient reaction time is from one-half to 48 hours, preferably one-half to four hours, and reaction temperatures from 20° to 100° C, preferably 40° to 80° C. The reaction in each individual case is performed preferably at the lowest temperature at which the reaction proceeds smoothly and expeditiously with a minimum of decomposition.

In the case where the starting material is one of formula II in which $X^1$ is —S—$SO_3$—Na or —S—$SO_3$—K, it is preferable to have at least one equivalent of water present in the reaction mixture. This water may be added directly to the reaction or it may be included as part of the acid catalyst. Examples of the latter instance would be when p-toluenesulfonic acid containing water of crystallization or concentrated hydrochloric acid are employed as the acid catalyst.

With reference to the preparation of the indenopyran- and indenothiopyranalkylamine derivatives of formula I$a$, the replacement of the starting material of formula II in any of the aforementioned processes (a) to (g) with the starting material of formula II$a$,

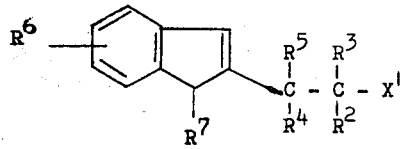

II a in which $R^2$, $R^3$, $R^4$, $R^5$, $R^6$, $R^7$ and $X^1$ is as defined in the first instance, gives the corresponding intermediate of formula X$a$,

X a in which $R^1$, $R^2$, $R^3$, $R^4$, $R^5$, $R^6$, $R^7$, X and $Y^1$ are as defined hereinbefore. In the case where $Y^1$ of said intermediate is $AlkNR^8R^9$, the intermediate is the indenopyran- or indenothiopyranalkylamine derivative of formula I$a$. In the case where $Y^1$ of said intermediate is other than $AlkNR^8R^9$, the intermediate is transformed to the corresponding indenopyran- or indenothiopyranalkylamine of formula I$a$ by the application of the steps described hereinbefore for effecting the corresponding transformation of intermediates of formula X to the compounds of formula I.

In other words the treatment of the starting material of formula II$a$ with a compound of formula $$R^1-\overset{\overset{O}{\|}}{C}-Y^1 \qquad (IX)$$

in which $R^1$ and $Y^1$ are as defined in the first instance according to the conditions of the condensation (II + IX → X), described hereinbefore, gives the corresponding intermediate of formula X$a$, the latter compound being the corresponding indenopyran- and indenothiopyranalkylamine of formula I$a$ or an intermediate therefor.

The requisite starting material of formula II$a$ in which $X^1$ is hydroxy and $R^2$, $R^3$, $R^4$, $R^5$, $R^6$ and $R^7$ are hydrogen is obtained readily by reduction of indene-2-acetic acid, H. Ahmed and N. Campbell, J. Chem. Soc., 4115 (1960) with lithium aluminum hydride.

The requisite starting material of formula II$a$ in which $X^1$ is hydroxy, and $R^2$ and $R^3$ are hydrogen and $R^4$, $R^5$, $R^6$ and $R^7$ are as defined in the first instance are prepared by oxidizing the aforementioned appropriate indene derivative of formula VII with hydrogen peroxide in the presence of formic acid according to the procedure of J. E. Horan and R. W. Schiessler, Organic Synthesis, 41, 53 (1961) to obtain the corresponding 2-indanone. Treatment of the latter compound with the appropriate Reformatski reagent of formula $ZCR^4R^5COOR^{18}$ in which Z is bromine or chlorine, $R^{18}$ is lower alkyl and $R^4$ and $R^5$ are as described in the first instance, followed by dehydration with phosphorous oxychloride of the lower alkyl ester of the resulting 2-hydroxyindane-2-acetic acid derivative gives the corresponding lower alkyl ester of the indene-2-acetic acid derivative. Hydrolysis of the latter derivative with sodium or potassium hydroxide gives the corresponding indene-2-acetic acid derivative. Reduction of the latter with lithium aluminum hydride yields the desired starting material of formula II$a$.

Alternatively, the starting material of formula II$a$ in which $X^1$ is hydroxy, $R^2$ and $R^3$ are hydrogen and $R^4$, $R^5$, $R^6$ and $R^7$ are as defined in the first instance is obtained by treating the appropriately substituted indanone of formula IV with about one molar equivalent of butyllithium, followed by treatment with the appropriate reagent of formula $ZCR^4CR^5COOR^{18}$, described above, to obtain the corresponding lower alkyl ester of the 1-oxoindane-2-acetic acid derivative. Reduction of the latter derivative with lithium aluminum hydride followed by dehydration with sulfuric acid in ethanol of the resulting 1-hydroxyindane-2-ethanol derivative gives the desired starting material of formula II$a$ ($R^2$ and $R^3$ = H).

The requisite starting material of formula II$a$ in which $X^1$ is hydroxyl and $R^2$, $R^3$, $R^4$, $R^5$, $R^6$ and $R^7$ are as defined in the first instance is available also by general synthesis involving the treatment of an appropriately substituted indanone of formula IV with about a molar equivalent of butyllithium in an inert solvent, preferbly ether, followed by treatment with the appropriate ethylene oxide derivative of formula VIII to obtain the corresponding 2-(hydroxyethyl)-1-indanone derivative. Reduction of the latter derivative with lithium aluminum hydride followed by dehydration with sulfuric acid in ethanol of the resulting 1-hydroxyindane-2-ethanol derivative as described previously gives the desired starting materials of formula II$a$.

The requisite starting material of formula IIa in which $X^1$ is mercapto, —S—SO$_3$—Na or —S—SO$_3$—K is obtained from the corresponding starting material of formula IIa in which $X^1$ is hydroxy in the same manner as described above for transforming the starting material of formula II in which $X^1$ is hydroxyl to the corresponding starting material of formula II in which $X^1$ is mercapto, —S—SO$_3$—Na and —S—SO$_3$—K.

The following examples illustrate further this invention.

EXAMPLE 1

Indene-3-ethanethiol (II; $R^2$, $R^3$, $R^4$, $R^5$, $R^6$ and $R^7$ = H and $X^1$ = H)

3-(2-Bromoethyl)-indene (17 g) is subjected to reflux for 3 hr. with a solution of 13.3 g of sodium thiosulfate in 100 ml of water and 200 ml of ethanol. The solvents are removed under reduced pressure to give the corresponding sodium indeneethyl thiosulfate derivative (II; $R^2$, $R^3$, $R^4$, $R^5$, $R^6$ and $R^7$ = H and $X^1$ = S—SO$_3$—Na). The latter compound is dissolved in a solution of NaOH (15 g) in 100 ml of water. Ethanol (300 ml is added) The solution is heated to reflux for 2 hr., allowed to cool, and extracted with three portions of ether. The combined extracts are washed with saturated brine solution, and concentrated. The residue is passed through a column packed with silica gel and eluted with benzene-hexane (1:3) to yield bis-[ω-(3-indenyl)ethyl]disulfide, nmr (CDCl$_3$): δ3.02 (s, 8H), 3.33 (m, 4H), 6.25 (m, 2H), 7.30 (m, 8H), as an oil. The latter compound (12 g) in anhydrous ether is added dropwise with efficient stirring to a suspension of lithium aluminium hydride (2.5 g) in ether (200 ml). The reaction mixture is stirred at room temp. overnight, decomposed with 10 ml of water, and the precipitate collected on a filter. The filtrate is dried (MgSO$_4$). Evaporation of the solution gives the title compound, nmr (CDCl$_3$) δ 1.48 (t, 1H), 2.83 (m, 4H), 3.32 (m, 2H), 6.25 (m, 1H), 7.30 (m, 4H).

By following the procedure of this example other starting materials of formula II ($X^1$ = SH or S—SO$_3$—Na, for example those described in Examples 56 to 106 are prepared by the appropriate choice of the appropriately substituted 3-(2-bromoethyl)-indene derivative prepared from their corresponding starting material of formula II ($X^1$ = OH) by treatment with phosphorus tribromide in carbon tetrachloride.

For example, by replacing 3-(2-bromoethyl)-indene in the procedure of this example with an equivalent amount of 3-(2-bromoethyl)-5-methoxy-indene, 5-methoxyindene-3-ethanethiol is obtained. Likewise, by replacing 3-(2-bromoethyl)-indene with 3-(2-bromo-1-methylpropyl)-indene, α,β-dimethylindene-3-ethanethiol is obtained.

EXAMPLE 2

1-Methyl-1,3,4,9-tetrahydroindeno[2,1-c]-pyran-1-acetic acid (X; $R^1$ = CH$_3$, $R^2$, $R^3$, $R^4$, $R^5$, $R^6$ and $R^7$ = H, X = O and $Y^1$ = CH$_2$COOH)

To a solution of indene-3-ethanol (8 g) and methyl acetoacetate (6 g) in 250 ml of dry benzene containing hydrated alkali-aluminum silicate (Molecular Sieves No. 4, about 2 g) is added 1 ml of boron trifluoride-etherate and the mixture stirred at room temperature for 4 hr. An additional 1 ml of boron trifluoride-etherate is added, the reaction mixture is stirred at ambient temperature overnight and then heated at reflux for 1 hr. The hydrated alkali-aluminum silicate is collected and the filtrate washed with 10% solution of sodium bicarbonate and water. After drying over magnesium sulfate the benzene is removed under reduced pressure affording 1-methyl-1,3,4,9-tetrahydroindeno[2,1-c]pyran-1-acetic acid methyl ester, $\nu_{max}^{film}$ 1724 cm$^{-1}$.

Hydrolysis of this ester to the title compound is effected as follows: The latter ester (11.5 g) is dissolved in 400 ml of methanol and the solution mixed with a solution of 12 g of sodium hydroxide in 100 ml of water. The resulting mixture is kept at room temperature overnight. Methanol is removed by evaporation. The residue is diluted with water. The aqueous solution is extracted repeatedly with ether, and acidified with 6N hydrochloric acid. The resulting precipitate is extracted with ether. The ether extract is dried (MgSO$_4$), filtered and concentrated. The residue is crystallized from benzene to give the title compound, m.p. 179°–180° C, nmr (CDCl$_3$) δ 1.45 (s, 3H), 2.51 (m, 2H), 2.73 (s, 2H), 3.25 (t, 2H), 4.02 (t, 2H), 7.26 (m, 4H), 9.80 (broad, 1H).

An equivalent amount of ethyl acetoacetate may replace methyl acetoacetate in the procedure of this example. In this case, 1-methyl-1,3,4,9-tetrahydroindeno[2,1-c]pyran-1-acetic acid ethyl ester is obtained as the ester.

An equivalent amount of propyl acetoacetate may replace methyl acetoacetate in the procedure of this example. In this case, 1-methyl-1,3,4,9-tetrahydroindeno[2,1-c]pyran-1-acetic acid propyl ester is obtained as the ester.

EXAMPLE 3

1-Methyl-1,3,4,9-tetrahydroindeno[2,1-c]pyran-1-propionic acid (X; $R^1$ = CH$_3$, $R^2$, $R^3$, $R^4$, $R^5$, $R^6$ and $R^7$ = H, X = O and $Y^1$ = CH$_2$CH$_2$COOH)

A mixture of indene-3-ethanol (15 g), dry benzene (300 ml), levulinic acid (22.6 g), boron trifluoride etherate (3 ml) and hydrated alkali-aluminum silicate (Molecular Sieves No. 4) is stirred at ambient temperature for 2 hr.

The reaction mixture is filtered. The filtrate is washed three times with 5N NaOH; the combined aqueous phase is washed twice with ether and then rendered acidic with cold diluted HCl. The aqueous phase is extracted with chloroform. The chloroform extract is dried (Na$_2$SO$_4$) and evaporated to dryness. The residue is crystallized from ether-hexane to afford the title compound, m.p. 97°–99° C, $\nu_{max}^{CHCl_3}$1700, nmr (CDCl$_3$) δ1.4 (s, 3H), 2.2 (m, 4H), 2.5 (m, 2H), 3.25 (t, 2H).

EXAMPLE 4

1-Methyl-1,3,4,9-tetrahydroindeno[2,1-c]thiopyran-1-acetic acid (X; $R^1$ = CH$_3$, $R^2$, $R^3$, $R^4$, $R^5$, $R^6$ and $R^7$ = H, X = S and $Y^1$ = CH$_2$COOH)

A mixture of indene-3-ethanethiol (8.0 g), methyl acetoacetate (6 g) and p-toluenesulfonic acid (0.8 g) in benzene (200 ml) is heated at reflux using a water separator for 5 hr. After cooling, the reaction mixture is washed with 10% solution of sodium bicarbonate and water. The benzene is removed under reduced pressure. The residue is the corresponding methyl ester of the title compound, 1-methyl-1,3,4,9-tetrahydroindeno[2,1-c]thiopyran-1-acetic acid methyl ester, $\nu_{max}^{CHCl_3}$1730 cm$^{-1}$.

The latter ester is dissolved in 200 ml of methanol and the 100 ml of 1.25 N NaOH is added. After stirring under reflux for 3 hr., the methanol is removed by evaporation and the aqueous residue extracted with ether. The aqueous-layer is then rendered acidic with 6N HCl and extracted with ether. The ether extract is dried ($MgSO_4$), filtered and evaporated to dryness. The residue is crystallized from ether to afford the title compound, m.p. 119°–121° C, $\nu_{max}^{CHCl_3}$ 3000, 1700 $cm^{-1}$.

The procedure of Examples 2 or 4 are followed to prepare other compounds of formula X in which $R^1$, $R^2$, $R^3$, $R^4$, $R^5$, $R^6$, $R^7$ and X are as defined in the first instance and $Y^1$ is $COOR^{19}$ or $Alk^1$—$COOR^{19}$ wherein $R^{19}$ and $Alk^1$ are as defined in the first instance. Examples of such compounds of formula X are listed in Tables I and II. In each of these examples an equivalent amount of the starting material of formula II listed therein is used instead of the starting material of formula II described in the procedures of Examples 2 and 4. Note that in each of these examples the ester obtained prior to hydrolysis is a corresponding ester compound of formula X.

Similarly, the procedure of Example 3 may be used to prepare the products listed in Tables I and II. In this case an equivalent amount of the starting material of formula II, listed therein, is used instead of the starting material of formula II described in Example 3 together with an equivalent amount of the requisite ketoacid.

TABLE I

| EX. | STARTING MATERIAL OF FORMULA II IN WHICH $X^1$ IS OH | | | | | | KETOESTER OF FORMULA $R^1-\overset{O}{\underset{\|}{C}}-Alk^1-CO-OR^{19}$ | | | PRODUCT: (PREFIX LISTED BELOW)-1,3,4,9-tetrahydroindeno-[2,1-c]pyran-1-(SUFFIX LISTED BELOW) |
|---|---|---|---|---|---|---|---|---|---|---|
| | $R^2$ | $R^3$ | $R^4$ | $R^5$ | $R^6$ | $R^7$ | $R^1$ | $Alk^1$-CO | $R^{19}$ | PREFIX//SUFFIX |
| 5 | H | H | H | H | H | H | $CH_3$ | CO | $C_2H_5$ | 1-methyl//carboxylic acid, m.p. 141–143° C |
| 6 | $CH_3$ | H | H | H | H | H | $C_2H_5$ | CO | $C_2H_5$ | 1-ethyl-3-methyl//carboxylic acid |
| 7 | i-$C_3H_7$ | H | H | H | 5-$CH_3$ | $CH_3$ | i-$C_3H_7$ | CO | $CH_3$ | 1,3-diisopropyl-6,9-dimethyl//carboxylic acid |
| 8 | $CH_3$ | $CH_3$ | H | H | 5-OH | H | $CH_3$ | CO | $CH_3$ | 6-hydroxy-1,3,3-trimethyl//carboxylic acid |
| 9 | H | H | H | H | 7-$C_2H_5$ | $C_2H_5$ | n-$C_3H_7$ | CO | $CH_3$ | 8,9-diethyl-1-propyl//carboxylic acid |
| 10 | H | H | i-$C_3H_7$ | H | H | i-$C_3H_7$ | n-$C_4H_9$ | CO | $CH_3$ | 1-butyl-4,9-diisopropyl//carboxylic acid |
| 11 | $CH_3$ | $CH_3$ | $C_2H_5$ | $C_2H_5$ | H | $C_2H_5$ | n-$C_4H_9$ | CO | $CH_3$ | 1-butyl-4,4,9-triethyl-3,3-dimethyl//carboxylic acid |
| 12 | H | H | $CH_3$ | H | H | H | $CH_3$ | $CH_2CO$ | $C_2H_5$ | 1,4-dimethyl//acetic acid |
| 13 | H | H | H | H | H | H | $C_2H_5$ | $CH_2CO$ | $C_2H_5$ | 1-ethyl//acetic acid |
| 14 | H | H | H | H | H | H | n-$C_3H_7$ | $CH_2CO$ | $C_2H_5$ | 1-propyl//acetic acid m.p. 131–133° C |
| 15 | H | H | H | H | H | H | i-$C_3H_7$ | $CH_2CO$ | $C_2H_5$ | 1-isopropyl//acetic acid |
| 16 | $CH_3$ | H | H | H | H | H | n-$C_3H_7$ | $CH_2CO$ | $C_2H_5$ | 3-methyl-1-propyl//acetic acid |
| 17 | $CH_3$ | H | $C_2H_5$ | H | H | $CH_3$ | $C_2H_5$ | $CH_2CO$ | $C_2H_5$ | 1,4-diethyl-3,9-dimethyl//acetic acid |
| 18 | H | H | H | H | H | $CH_3$ | $CH_3$ | $CH(CH_3)CO$ | $C_2H_5$ | α,1,9-trimethyl//acetic acid |
| 19 | H | H | H | H | H | $C_2H_5$ | n-$C_4H_9$ | $C(CH_3)_2CO$ | $C_2H_5$ | 1-butyl-9-ethyl-α,α-dimethyl//acetic acid |
| 20 | H | H | H | H | H | H | t-$C_4H_9$ | $CH_2CO$ | $C_2H_5$ | 1-t-butyl//acetic acid |
| 21 | H | H | H | H | H | H | n-$C_4H_9$ | $CH_2CO$ | $C_2H_5$ | 1-butyl//acetic acid |
| 22 | H | H | H | H | 7-$CH_3$ | $C_2H_5$ | n-$C_3H_7$ | $CH_2CO$ | $C_2H_5$ | 9-ethyl-8-methyl-1-propyl//acetic acid |
| 23 | H | H | H | H | 5-Br | $C_2H_5$ | $C_2H_5$ | $CH_2CO$ | $C_2H_5$ | 6-bromo-1,9-diethyl//acetic acid |
| 24 | H | H | H | H | 5-$CH_3$ | H | $CH_3$ | $CH_2CO$ | $CH_3$ | 1,6-dimethyl//acetic acid |
| 25 | H | H | H | H | 5-$OCOCH_3$ | t-$C_4H_9$ | $CH_3$ | $CH_2CO$ | $C_2H_5$ | 6-acetoxy-9-t-butyl-1-methyl//acetic acid |
| 26 | H | H | H | H | 5-benzyloxy | i-$C_3H_7$ | $CH_3$ | $CH_2CO$ | $C_2H_5$ | 6-benzyloxy-9-isopropyl-1-methyl//acetic acid |
| 27 | H | H | H | H | 4-$CH_3$ | $CH_3$ | n-$C_3H_7$ | $CH_2CO$ | $C_2H_5$ | 5,9-dimethyl-1-propyl//acetic acid |
| 28 | H | H | H | H | 6-$CH_3$ | H | n-$C_3H_7$ | $CH_2CO$ | $C_2H_5$ | 7-methyl-1-propyl//acetic acid |
| 29 | H | H | H | H | 5-$NO_2$ | n-$C_3H_7$ | n-$C_3H_7$ | $CH_2CO$ | $C_2H_5$ | 1,9-dipropyl-6-nitro//acetic acid |
| 30 | H | H | $CH_3$ | $CH_3$ | H | $CH_3$ | n-$C_3H_7$ | $CH_2CO$ | $C_2H_5$ | 4,4,9-trimethyl-1-propyl//acetic acid |
| 31 | $CH_3$ | $CH_3$ | H | H | 5-$OC_2H_5$ | H | $C_2H_5$ | $CH(C_2H_5)CO$ | $C_2H_5$ | 3,3-dimethyl-6-ethoxy-α,α,1-triethyl//acetic acid |

TABLE I-continued

| EX. | STARTING MATERIAL OF FORMULA II IN WHICH $X^1$ IS OH | | | | | | KETOESTER OF FORMULA $R^1-\overset{O}{\underset{\|}{C}}-Alk^1-CO-OR^{19}$ | | | PRODUCT: (PREFIX LISTED BELOW)-1,3,4,9-tetrahydroindeno-[2,1-c]pyran-1-(SUFFIX LISTED BELOW) |
|---|---|---|---|---|---|---|---|---|---|---|
| | $R^2$ | $R^3$ | $R^4$ | $R^5$ | $R^6$ | $R^7$ | $R^1$ | $Alk^1$-CO | $R^{19}$ | PREFIX//SUFFIX |
| 32 | $CH_3$ | $CH_3$ | $C_2H_5$ | $C_2H_5$ | 6-$C_2H_5$ | n-$C_4H_9$ | n-$C_4H_9$ | $C(CH_3)_2CO$ | $C_2H_5$ | 1,9-dibutyl-α,α,3,3-tetramethyl-4,4,7-triethyl//acetic acid |
| 33 | $CH_3$ | H | n-$C_3H_7$ | n-$C_3H_7$ | 4-n-$C_3H_7$ | $CH_3$ | $C_2H_5$ | $CH(CH_3)CO$ | $C_2H_5$ | 1-ethyl-α,3,9-trimethyl-4,4,9-tripropyl//acetic acid |
| 34 | H | H | H | H | H | H | n-$C_3H_7$ | $C(CH_3)_2CO$ | $C_2H_5$ | α,α-dimethyl-1-propyl//acetic acid |
| 35 | $C_2H_5$ | $C_2H_5$ | $C_2H_5$ | $C_2H_5$ | 4-$C_2H_5$ | $C_2H_5$ | t-$C_4H_9$ | $C(i-C_3H_7)_2CO$ | $C_2H_5$ | 1-t-butyl-α,α-diisopropyl-3,3,4,4,5,9-hexaethyl//acetic acid |
| 36 | H | H | H | H | 4-I | $CH_3$ | i-$C_3H_7$ | $CH_2CH_2CO$ | $C_2H_5$ | 9-methyl-5-iodo-1-isopropyl//propionic acid |
| 37 | $CH_3$ | $CH_3$ | $CH_3$ | $CH_3$ | 7-$OCCH_3$ (O) | $C_2H_5$ | $C_2H_5$ | $CH_2CH(CH_3)CO$ | $C_2H_5$ | 8-acetoxy-1,9-diethyl-α,3,3,4,4-pentamethyl//propionic acid |
| 38 | H | H | H | H | 6-OH | $CH_3$ | n-$C_3H_7$ | $CH_2C(C_2H_5)_2CO$ | $C_2H_5$ | β,β-diethyl-7-hydroxy-9-methyl-1-propyl//propionic acid |
| 39 | $CH_3$ | H | H | H | 7-$NO_2$ | $CH_3$ | n-$C_4H_9$ | $CH(n-C_3H_7)CH_2CO$ | $C_2H_5$ | 1-butyl-3,9-dimethyl-8-nitro-β-propyl//propionic acid |
| 40 | H | H | $CH_3$ | H | 5-$CH_3$ | $CH_3$ | n-$C_4H_9$ | $C(CH_3)_2C(CH_3)_2CO$ | $C_2H_5$ | 1-butyl-α,α,β,β,4,6,9-heptamethyl//propionic acid |
| 41 | $CH_3$ | H | H | H | H | $CH_3$ | $CH_3$ | $CH_2C(n-C_3H_7)_2CO$ | $C_2H_5$ | 1,3,9-trimethyl-α,α-dipropyl//propionic acid |
| 42 | $CH_3$ | H | $C_2H_5$ | $C_2H_5$ | H | $CH_3$ | $C_2H_5$ | $CH(CH_3)C(CH_3)_2CO$ | $CH_3$ | α,α,β,3,9-pentamethyl-1,4,4-triethyl//propionic acid |
| 43 | H | H | $CH_3$ | $CH_3$ | H | $C_2H_5$ | $C_2H_5$ | $C(CH_3)_2CH_2CO$ | $CH_3$ | 1,9-diethyl-β,β,4,4-tetramethyl//propionic acid |
| 44 | H | H | n-$C_3H_7$ | H | 4-$OCC_2H_5$ (O) | $CH_3$ | $CH_3$ | $C(C_2H_5)_2C(C_2H_5)CO$ | $CH_3$ | 1,9-dimethyl-5-propionoxy-4-propyl-α,β,β-triethyl//propionic acid |
| 45 | n-$C_3H_7$ | H | H | H | 4-$OCH_3$ | $CH_3$ | n-$C_3H_7$ | $CH_2CH(CH_3)CO$ | $C_2H_5$ | α,9-dimethyl-1,3-dipropyl-5-methoxy//propionic acid |
| 46 | $C_2H_5$ | H | H | H | 5-$NO_2$ | $CH_3$ | $CH_3$ | $[C(C_2H_5)]_2CC$ | $C_2H_5$ | 1,9-dimethyl-6-nitro-α,α,β,β,3-pentaethyl//propionic acid |
| 47 | $C_2H_5$ | $C_2H_5$ | H | H | 4-$C_2H_5$ | $C_2H_5$ | n-$C_3H_7$ | $CH(n-C_3H_7)CH_2CO$ | $CH_3$ | β,1-dipropyl-3,3,5,9-tetraethyl//propionic acid |
| 48 | H | H | H | H | 6-$OC_2H_5$ | $C_2H_5$ | n-$C_4H_9$ | $[CH(C_2H_5)]_2CO$ | $C_2H_5$ | 1-butyl-7-ethoxy-α,β,9-triethyl//propionic acid |
| 49 | H | H | H | H | H | H | $CH_3$ | $CH_2CH_2CH_2CO$ | $C_2H_5$ | 1-methyl//butyric acid |
| 50 | $CH_3$ | H | H | H | H | $CH_3$ | $C_2H_5$ | $CH(CH_3)CH_2CH_2CO$ | $C_2H_5$ | 1-ethyl-γ,3,9-trimethyl//butyric acid |
| 51 | $CH_3$ | $CH_3$ | H | H | H | $CH_3$ | n-$C_3H_7$ | $C(C_2H_5)_2(CH_2)_2CO$ | $C_2H_5$ | γ,γ-diethyl-1-propyl-3,3,9-trimethyl//butyric acid |
| 52 | $C_2H_5$ | H | H | H | 6-$NO_2$ | H | n-$C_4H_9$ | $[CH(CH_3)]_3CO$ | $C_2H_5$ | 1-butyl-3-ethyl-7-nitro-α,β,γ-trimethyl//butyric acid |
| 53 | $CH_3$ | $CH_3$ | H | H | 4-n-$C_3H_7$ | n-$C_3H_7$ | n-$C_3H_7$ | $CH_2[CH(C_2H_5)]_2CO$ | $C_2H_5$ | α,β-diethyl-3,3-dimethyl-1,5,9-tripropyl//butyric acid |
| 54 | H | H | H | H | 7-OH | n-$C_4H_9$ | $C_2H_5$ | $C(CH_3)_2-CH_2C(CH_3)_2CO$ | $C_2H_5$ | 9-butyl-1-ethyl-8-hydroxy-α,α,γ,γ-tetramethyl//butyric acid |
| 55 | $CH_3$ | H | $CH_3$ | H | 4-$OC_2H_5$ | t-$C_4H_9$ | $C_2H_5$ | $[C(CH_3)_2]_3CO$ | $C_2H_5$ | 9-t-butyl-5-ethoxy-1-ethyl-α,α,β,β,γ,γ,3,4-octamethyl//butyric acid |

TABLE II

| EX. | STARTING MATERIAL OF FORMULA II IN WHICH X¹ IS SH | | | | | | KETOESTER OF FORMULA $R^1-\overset{O}{\underset{\|}{C}}-Alk^1-CO-OR^{19}$ | | | PRODUCT: (PREFIX LISTED BELOW)-1,3,4,9-tetrahydroindeno-[2,1-c]thiopyran-1-(SUFFIX LISTED BELOW) |
|---|---|---|---|---|---|---|---|---|---|---|
| | $R^2$ | $R^3$ | $R^4$ | $R^5$ | $R^6$ | $R^7$ | $R^1$ | $Alk^1$-CO | $R^{19}$ | PREFIX//SUFFIX |
| 56 | H | H | H | H | H | H | $CH_3$ | CO | $C_2H_5$ | 1-methyl//carboxylic acid |
| 57 | $CH_3$ | H | H | H | H | H | $C_2H_5$ | CO | $C_2H_5$ | 1-ethyl-3-methyl//carboxylic acid |
| 58 | i-$C_3H_7$ | H | H | H | 5-$CH_3$ | $CH_3$ | i-$C_3H_7$ | CO | $CH_3$ | 1,3-diisopropyl-6,9-dimethyl//carboxylic acid |
| 59 | $CH_3$ | $CH_3$ | H | H | 5-OH | H | $CH_3$ | CO | $CH_3$ | 6-hydroxy-1,3,3-trimethyl//carboxylic acid |
| 60 | H | H | H | H | 7-$C_2H_5$ | $C_2H_5$ | n-$C_3H_7$ | CO | $CH_3$ | 8,9-diethyl-1-propyl//carboxylic acid |
| 61 | H | H | i-$C_3H_7$ | H | H | i-$C_3H_7$ | n-$C_4H_9$ | CO | $CH_3$ | 1-butyl-4,9-diisopropyl//carboxylic acid |
| 62 | $CH_3$ | $CH_3$ | $C_2H_5$ | $C_2H_5$ | H | $C_2H_5$ | n-$C_4H_9$ | CO | $CH_3$ | 1-butyl-4,4,9-triethyl-3,3-dimethyl//carboxylic acid |
| 63 | H | H | $CH_3$ | H | H | H | $CH_3$ | $CH_2CO$ | $C_2H_5$ | 1,4-dimethyl//acetic acid |
| 64 | H | H | H | H | H | H | $C_2H_5$ | $CH_2CO$ | $C_2H_5$ | 1-ethyl//acetic acid |
| 65 | H | H | H | H | H | H | n-$C_3H_7$ | $CH_2CO$ | $C_2H_5$ | 1-propyl//acetic acid |
| 66 | H | H | H | H | H | H | i-$C_3H_7$ | $CH_2CO$ | $C_2H_5$ | 1-isopropyl//acetic acid |
| 67 | $CH_3$ | H | H | H | H | H | n-$C_3H_7$ | $CH_2CO$ | $C_2H_5$ | 3-methyl-1-propyl//acetic acid |
| 68 | $CH_3$ | H | $C_2H_5$ | H | H | $CH_3$ | $C_2H_5$ | $CH_2CO$ | $C_2H_5$ | 1,4-diethyl-3,9-dimethyl//acetic acid |
| 69 | H | H | H | H | H | $CH_3$ | $CH_3$ | $CH(CH_3)CO$ | $C_2H_5$ | α,1,9-trimethyl//acetic acid |
| 70 | H | H | H | H | H | $C_2H_5$ | n-$C_4H_9$ | $C(CH_3)_2CO$ | $C_2H_5$ | 1-butyl-9-ethyl-α,α-dimethyl//acetic acid |
| 71 | H | H | H | H | H | H | t-$C_4H_9$ | $CH_2CO$ | $C_2H_5$ | 1-t-butyl//acetic acid |
| 72 | H | H | H | H | H | H | n-$C_4H_9$ | $CH_2CO$ | $C_2H_5$ | 1-butyl//acetic acid |
| 73 | H | H | H | H | 7-$CH_3$ | $C_2H_5$ | n-$C_3H_7$ | $CH_2CO$ | $C_2H_5$ | 9-ethyl-8-methyl-1-propyl//acetic acid |
| 74 | H | H | H | H | 5-Br | $C_2H_5$ | $C_2H_5$ | $CH_2CO$ | $C_2H_5$ | 6-bromo-1,9-diethyl//acetic acid |
| 75 | H | H | H | H | 5-$CH_3$ | H | $CH_3$ | $CH_2CO$ | $CH_3$ | 1,6-dimethyl//acetic acid |
| 76 | H | H | H | H | 5-$OCOCH_3$ | t-$C_4H_9$ | $CH_3$ | $CH_2CO$ | $C_2H_5$ | 6-acetoxy-9-t-butyl-1-methyl//acetic acid |
| 77 | H | H | H | H | 5-benzyloxy | i-$C_3H_7$ | $CH_3$ | $CH_2CO$ | $C_2H_5$ | 6-benzyloxy-9-isopropyl-1-methyl//acetic acid |
| 78 | H | H | H | H | 4-$CH_3$ | $CH_3$ | n-$C_3H_7$ | $CH_2CO$ | $C_2H_5$ | 5,9-dimethyl-1-propyl//acetic acid |
| 79 | H | H | H | H | 6-$CH_3$ | H | n-$C_3H_7$ | $CH_2CO$ | $C_2H_5$ | 7-methyl-1-propyl//acetic acid |
| 80 | H | H | H | H | 5-$NO_2$ | n-$C_3H_7$ | n-$C_3H_7$ | $CH_2CO$ | $C_2H_5$ | 6-nitro-1,9-dipropyl//acetic acid |
| 81 | H | H | $CH_3$ | $CH_3$ | H | $CH_3$ | n-$C_3H_7$ | $CH_2CO$ | $C_2H_5$ | 4,4,9-trimethyl-1-propyl//acetic acid |
| 82 | $CH_3$ | $CH_3$ | H | H | 5-$OC_2H_5$ | H | $C_2H_5$ | $CH(C_2H_5)CO$ | $C_2H_5$ | 3,3-dimethyl-6-ethoxy-α,α,1-triethyl//acetic acid |
| 83 | $CH_3$ | $CH_3$ | $C_2H_5$ | $C_2H_5$ | 6-$C_2H_5$ | n-$C_4H_9$ | n-$C_4H_9$ | $C(CH_3)_2CO$ | $C_2H_5$ | 1,9-dibutyl-α,α,3,3-tetramethyl-4,4,7-triethyl//acetic acid |
| 84 | $CH_3$ | H | n-$C_3H_7$ | n-$C_3H_7$ | 4-n-$C_3H_7$ | $CH_3$ | $C_2H_5$ | $CH(CH_3)CO$ | $C_2H_5$ | 1-ethyl-α,3,9-trimethyl-4,4,9-tripropyl//acetic acid |
| 85 | H | H | H | H | H | H | n-$C_3H_7$ | $C(CH_3)_2CO$ | $C_2H_5$ | α,α-dimethyl-1-propyl//acetic acid |
| 86 | $C_2H_5$ | $C_2H_5$ | $C_2H_5$ | $C_2H_5$ | 4-$C_2H_5$ | $C_2H_5$ | t-$C_4H_9$ | $C(i-C_3H_7)_2CO$ | $C_2H_5$ | 1-t-butyl-α,α-diisopropyl-3,3,4,4,5,9-hexaethyl//acetic acid |
| 87 | H | H | H | H | H | H | $CH_3$ | $CH_2CH_2CO$ | $C_2H_5$ | 1-methyl//propionic acid |
| 88 | $CH_3$ | $CH_3$ | $CH_3$ | $CH_3$ | 7-$OCCH_3$ (O) | $C_2H_5$ | $C_2H_5$ | $CH_2CH(CH_3)CO$ | $C_2H_5$ | 8-acetoxy-1,9-diethyl-α,3,3,4,4-pentamethyl//propionic acid |
| 89 | H | H | H | H | 6-OH | $CH_3$ | n-$C_3H_7$ | $CH_2C(C_2H_5)_2CO$ | $C_2H_5$ | β,β-diethyl-7-hydroxy-9-methyl-1-propyl//propionic acid |
| 90 | $CH_3$ | H | H | H | 7-$NO_2$ | $CH_3$ | n-$C_4H_9$ | $CH(n-C_3H_7)CH_2CO$ | $C_2H_5$ | 1-butyl-3,9-dimethyl-8-nitro-β-propyl//propionic acid |
| 91 | H | H | $CH_3$ | H | 5-$CH_3$ | $CH_3$ | n-$C_4H_9$ | $C(CH_3)_2C(CH_3)_2CO$ | $C_2H_5$ | 1-butyl-α,α,β,β,4,6,9- |

TABLE II-continued

| EX. | STARTING MATERIAL OF FORMULA II IN WHICH $X^1$ IS SH | | | | | | KETOESTER OF FORMULA $R^1-\overset{O}{\underset{\|}{C}}-Alk^1-CO-OR^{19}$ | | | PRODUCT: (PREFIX LISTED BELOW)-1,3,4,9-tetrahydroindeno-[2,1-c]thiopyran-1-(SUFFIX LISTED BELOW) |
|---|---|---|---|---|---|---|---|---|---|---|
| | $R^2$ | $R^3$ | $R^4$ | $R^5$ | $R^6$ | $R^7$ | $R^1$ | $Alk^1$-CO | $R^{19}$ | PREFIX//SUFFIX |
| 92 | $CH_3$ | H | H | H | H | $CH_3$ | $CH_3$ | $CH_2C(n-C_3H_7)_2CO$ | $C_2H_5$ | heptamethyl//propionic acid |
| | | | | | | | | | | 1,3,9-trimethyl-α,α-dipropyl//propionic acid |
| 93 | $CH_3$ | H | $C_2H_5$ | $C_2H_5$ | H | $CH_3$ | $C_2H_5$ | $CH(CH_3)C(CH_3)_2CO$ | $CH_3$ | α,α,β,3,9-pentamethyl-1,4,4-triethyl//propionic acid |
| 94 | H | H | $CH_3$ | $CH_3$ | H | $C_2H_5$ | $C_2H_5$ | $C(CH_3)_2CH_2CO$ | $CH_3$ | 1,9-diethyl-β,β,4,4-tetramethyl//propionic acid |
| 95 | H | H | n-$C_3H_7$ | H | 4-O$\overset{O}{\underset{\|}{C}}$C$_2$H$_5$ | $CH_3$ | $CH_3$ | $C(C_2H_5)_2C(C_2H_5)CO$ | $CH_3$ | 1,9-dimethyl-5-propionoxy-4-propyl-α,β,β-triethyl//propionic acid |
| 96 | n-$C_3H_7$ | H | H | H | 4-OCH$_3$ | $CH_3$ | n-$C_3H_7$ | $CH_2CH(CH_3)CO$ | $C_2H_5$ | α,9-dimethyl-1,3-dipropyl-5-methoxy//propionic acid |
| 97 | $C_2H_5$ | H | H | H | 5-NO$_2$ | $CH_3$ | $CH_3$ | $C(C_2H_5)_2C(C_2H_5)_2$-CO | $C_2H_5$ | 1,9-dimethyl-6-nitro-α,α,β,β,3-pentaethyl//propionic acid |
| 98 | $C_2H_5$ | $C_2H_5$ | H | H | 4-$C_2H_5$ | $C_2H_5$ | n-$C_3H_7$ | $CH(n-C_3H_7)CH_2CO$ | $CH_3$ | β,1-dipropyl-3,3,5,9-tetraethyl//propionic acid |
| 99 | $CH_3$ | $CH_3$ | H | H | H | $CH_3$ | n-$C_3H_7$ | $C(C_2H_5)_2CH_2CH_2CO$ | $C_2H_5$ | γ,γ-diethyl-1-propyl-3,3,9-trimethyl//butyric acid |
| 100 | H | H | H | H | 6-O$C_2H_5$ | $C_2H_5$ | n-$C_4H_9$ | $[CH(C_2H_5)]_2CO$ | $C_2H_5$ | 1-butyl-7-ethoxy-α,β,9-triethyl//propionic acid |
| 101 | H | H | H | H | H | H | $CH_3$ | $CH_2CH_2CH_2CO$ | $C_2H_5$ | 1-methyl//butyric acid |
| 102 | $CH_3$ | H | H | H | H | $CH_3$ | $C_2H_5$ | $CH(CH_3)CH_2CH_2CO$ | $C_2H_5$ | 1-ethyl-γ,3,9-trimethyl//butyric acid |
| 103 | $C_2H_5$ | H | H | H | 6-NO$_2$ | H | n-$C_4H_9$ | $[CH(CH_3)]_3CO$ | $C_2H_5$ | 1-butyl-3-ethyl-7-nitro-α,β,γ-trimethyl//butyric acid |
| 104 | $CH_3$ | $CH_3$ | H | H | 4-n-$C_3H_7$ | n-$C_3H_7$ | n-$C_3H_7$ | $CH_2[CH(C_2H_5)]_2CO$ | $C_2H_5$ | α,β-diethyl-3,3-dimethyl-1,5,9-tripropyl//butyric acid |
| 105 | H | H | H | H | 7-OH | n-$C_4H_9$ | $C_2H_5$ | $C(CH_3)_2$-$CH_2C(CH_3)_2CO$ | $C_2H_5$ | 9-butyl-1-ethyl-8-hydroxy-α,α,γ,γ-tetramethyl//butyric acid |
| 106 | $CH_3$ | H | $CH_3$ | H | 4-O$C_2H_5$ | t-$C_4H_9$ | $C_2H_5$ | $[C(CH_3)_2]_3CO$ | $C_2H_5$ | 9-t-butyl-5-ethoxy-1-ethyl-α,α,β,β,γ,γ,3,4-octamethyl//butyric acid |

EXAMPLE 107

N,N,1-Trimethyl-1,3,4,9-tetrahydroindeno[2,1-c]pyran-1-acetamide[X; $R^1 = CH_3$, $R^2$, $R^3$, $R^4$, $R^5$, $R^6$ and $R^7$ = H, X = O and $Y^1 = CH_2CON(CH_3)_2$]

Triethylamine (12.0 g) and then ethyl chloroformate (13 g) in 50 ml of tetrahydrofuran (THF) are added to a cooled solution (−5° C) of 1-methyl-1,3,4,9-tetrahydroindeno[2,1-c]-1-acetic acid (97 g), described in Example 2, in 150 ml. of THF. After being stirred for 90 minutes the mixture is further cooled to ca. −10° C. and treated with dimethylamine (230 ml of the 40% aqueous solution) and stirred at −10° C. for an additional 30 min. Most of the THF is evaporated and the residue partitioned between chloroform and water. The chloroform layer is washed with water, dried (MgSO$_4$) and concentrated to afford the title compound as an oil, $\nu_{max}^{CHCl_3}$ 1625, 1400, 1075 cm$^{-1}$, nmr (CDCl$_3$) δ 1.55 (s, 3H), 3.07 2.53 (m, 2H), 2.74 (s, 2H), 2.92 and 3.07 (s, 6H), 3.42 (m, 2H), 3.96 (t, 2H), 7.25 (m, 4H).

In the same manner but replacing the 40% aqueous solution of dimethylamine with an equivalent amount of the amines of formula HNR$^8$R$^9$, ammonium hydroxide (concentrated), methylamine (40% aqueous solution), n-hexylamine (20% aqueous solution), diethylamine (30% aqueous solution), isopropylamine (40% aqueous solution), ethylamine (70% aqueous solution), pyrrolidine (50% aqueous solution), piperidine, morpholine, N-methylpiperazine.

1-methyl-1,3,4,9-tetrahydroindeno[2,1-c]pyran-1-acetamide, m.p. 87°–88° C., $\nu_{max}^{CHCl_3}$ 3460, 3340, 1670 cm$^{-1}$, N,1-dimethyl-1,3,4,9-tetrahydroindeno[2,1-c]pyran-1-acetamide, m.p. 90°–91° C., $\nu_{max}^{CHCl_3}$ 3460, 3395, 1665cm$^{-1}$, N-hexyl-1-methyl-1,3,4,9-tetrahydroindeno[2,1-c]pyran-1-acetamide, N,N-diethyl-1-methyl-1,3,4,9-tetrahydroindeno[2,1-c]pyran-1-acetamide, 1-methyl-N-isopropyl-1,3,4,9-tetrahydroindeno[2,1-c]pyran-1-acetamide, N-ethyl-1-methyl-1,3,4,9-tetrahydroindeno[2,1-c]pyran-1-acetamide, 1-[(1-methyl-1,3,4,9-tetrahydroindeno[2,1-c]pyran-1-yl)acetyl]-pyrrolidine, 1-[(1-methyl-1,3,4,9-tetrahydroindeno[2,1-c]pyran-1-yl)acetyl]-piperidine, 4-[(1-methyl-1,3,4,9-tetrahydroindeno[2,1-c]pyran-1-yl)acetyl]morpholine, and 1-methyl-4-[(1-methyl-1,3,4,9-tetrahydroindeno[2,1-c]pyran-1-yl)acetyl]piperazine, are obtained, respectively.

By following the procedure of Example 107 but using as starting material an equivalent amount of one of the acid compounds of formula X, described in Examples 3 and 5 to 55, instead of 1-methyl-1,3,4,9-tetrahydroindeno[2,1-c]pyran-1-acetic acid, and using an equivalent amount of an appropriate amine such as ammonia or a primary or secondary amine described in Example 107, then the corresponding amide compound of formula X is obtained.

Examples of such amides are listed as products in Tables III and IV together with the appropriate starting material of formula II with the amine used for the preparation of the amide. In each case the starting material is noted by the example in which it is prepared.

TABLE III

| EX. | NO. OF THE EXAMPLE IN WHICH STARTING MATERIAL IS PREPARED | AMINE | PRODUCT: [(PREFIX LISTED BELOW)-1,3,4,9-TETRAHYDROINDENO[2,1-c]-PYRAN-1-(SUFFIX LISTED BELOW)] PREFIX//SUFFIX |
|---|---|---|---|
| 108 | 3 | $CH_3NH_2$ | N,1-dimethyl//propionamide |
| 109 | 3 | $NH_3$ | 1-methyl//propionamide |
| 110 | 3 | $(CH_3)_2NH$ | N,N,1-trimethyl//propionamide, nmr($CDCl_3$) δ 1.40 (3H), 2.14 (4H), 2.47 (2H), 2.85 and 2.89 (6H), 3.30 (2H), 3.95 (2H), 7.25 (4H) |
| 111 | 3 | $C_2H_5NH_2$ | N-ethyl-1-methyl//propionamide |
| 112 | 3 | $(C_2H_5)_2NH$ | N,N-diethyl-1-methyl//propionamide |
| 113 | 5 | $(CH_3)_2NH$ | N,N,1-trimethyl//carboxamide, nmr ($CDCl_3$) δ 1.68 (s, 3H), 2.65 (m,2H), 3.12 (s, 6H), 3.54 (m, 2H), 4.08 (m, 2H), 7.28 (m, 4H) |
| 114 | 5 | $NH_3$ | 1-methyl//carboxamide |
| 115 | 6 | $(CH_3)_2NH$ | 1-ethyl-N,N,3-trimethyl//carboxamide |
| 116 | 7 | $n-C_6H_{13}NH_2$ | 1,3-diisopropyl-6,9-dimethyl-N-hexyl//carboxamide |
| 117 | 8 | $C_2H_5NH_2$ | N-ethyl-6-hydroxy-1,3,3-trimethyl//carboxamide |
| 118 | 9 | $CH_3NH_2$ | 8,9-diethyl-N-methyl-1-propyl//carboxamide |
| 119 | 10 | $(CH_3)_2NH$ | 1-butyl-N,N-dimethyl-4,9-diisopropyl//carboxamide |
| 120 | 11 | $(CH_3)_2NH$ | 1-butyl-4,4,9-triethyl-N,N,3,3-tetramethyl//carboxamide |
| 121 | 12 | $CH_3NH_2$ | N,1,4-trimethyl//acetamide |
| 122 | 13 | $NH_3$ | 1-ethyl//acetamide |
| 123 | 13 | $(CH_3)_2NH$ | N,N-dimethyl-1-ethyl//acetamide |
| 124 | 13 | $n-C_6H_{13}NH_2$ | 1-ethyl-N-hexyl//acetamide |
| 125 | 13 | $(C_2H_5)_2NH$ | N,N,1-triethyl//acetamide |
| 126 | 14 | $CH_3NH_2$ | N-methyl-1-propyl//acetamide |
| 127 | 14 | $NH_3$ | 1-propyl//acetamide |
| 128 | 14 | $(CH_3)_2NH$ | N,N-dimethyl-1-propyl//acetamide |
| 129 | 14 | $n-C_6H_{13}NH_2$ | N-hexyl-1-propyl//acetamide |
| 130 | 14 | $(C_2H_5)_2NH$ | N,N-diethyl-1-propyl//acetamide |
| 131 | 15 | $CH_3NH_2$ | 1-isopropyl-N-methyl//acetamide |
| 132 | 15 | $(C_2H_5)_2NH$ | N,N-diethyl-1-isopropyl//acetamide |
| 133 | 16 | $CH_3NH_2$ | N,3-dimethyl-1-propyl//acetamide |
| 134 | 16 | $(CH_3)_2NH$ | 1-propyl-N,N,3-trimethyl//acetamide |
| 135 | 17 | $(C_2H_5)_2NH$ | 3,9-dimethyl-N,N,1,4-tetraethyl//acetamide |
| 136 | 18 | $CH_3NH_2$ | N,α,1,9-tetramethyl//acetamide |
| 137 | 18 | $NH_3$ | α,1,9-trimethyl//acetamide |
| 138 | 18 | $(CH_3)_2NH$ | N,N,α,1,9-pentamethyl//acetamide |
| 139 | 19 | $C_2H_5NH_2$ | 1-butyl-N,9-diethyl-α,α-dimethyl//acetamide |
| 140 | 20 | $CH_3NH_2$ | 1-t-butyl-N-methyl//acetamide |
| 141 | 21 | $CH_3NH_2$ | 1-butyl-N-methyl//acetamide |
| 142 | 22 | $C_2H_5NH_2$ | N,9-diethyl-8-methyl-1-propyl//acetamide |
| 143 | 23 | $(C_2H_5)_2NH$ | 6-bromo-N,N,1,9-tetraethyl//acetamide |
| 144 | 24 | $NH_3$ | 1,6-dimethyl//acetamide |
| 145 | 25 | $t-C_4H_9NH_2$ | 6-acetoxy-N,9-di-t-butyl-1-methyl//acetamide |
| 146 | 26 | $NH_3$ | 6-benzyloxy-9-isopropyl-1-methyl//acetamide |
| 147 | 27 | $(CH_3)_2NH$ | 1-propyl-N,N,5,9-tetramethyl//acetamide |
| 148 | 28 | $(C_2H_5)_2NH$ | N,N-diethyl-7-methyl-1-propyl//acetamide |
| 149 | 29 | $n-C_6H_{13}NH_2$ | 1,9-dipropyl-N-hexyl-6-nitro//acetamide |
| 150 | 30 | $CH_3NH_2$ | 1-propyl-N,4,4,9-tetramethyl//acetamide |
| 151 | 31 | $NH_3$ | 3,3-dimethyl-6-ethoxy-α,α,1-triethyl//acetamide |
| 152 | 32 | $C_2H_5NH_2$ | 1,9-dibutyl-α,α,3,3-tetramethyl-N,4,4,7-tetraethyl//acetamide |
| 153 | 33 | $CH_3NH_2$ | 1-ethyl-N,α,3,9-tetramethyl-4,4,9-tripropyl//acetamide |
| 154 | 34 | $(CH_3)_2NH$ | 1-propyl-N,N,α,α-tetramethyl//acetamide |

TABLE III-continued

| EX. | NO. OF THE EXAMPLE IN WHICH STARTING MATERIAL IS PREPARED | AMINE | PRODUCT: [(PREFIX LISTED BELOW)-1,3,4,9-TETRAHYDROINDENO[2,1-c]-PYRAN-1-(SUFFIX LISTED BELOW)] PREFIX//SUFFIX |
|---|---|---|---|
| 155 | 35 | $(C_2H_5)_2NH$ | 1-t-butyl-$\alpha,\alpha$-diisopropyl-N,N,3,3-4,4,5,9-octaethyl//acetamide |
| 156 | 36 | $CH_3NH_2$ | N,9-dimethyl-5-iodo-1-isopropyl//propionamide |
| 157 | 38 | $CH_3NH_2$ | $\beta,\beta$-diethyl-N,9-dimethyl-7-hydroxy-1-propyl//propionamide |
| 158 | 39 | $NH_3$ | 1-butyl-3,9-dimethyl-8-nitro-$\beta$-propyl//propionamide |
| 159 | 43 | $C_2H_5NH_2$ | $\beta,\beta,4,4$-tetramethyl-N,1,9-triethyl//propionamide |
| 160 | 45 | n-$C_3H_7NH_2$ | $\alpha,9$-dimethyl-5-methoxy-N,1,3-tripropyl//propionamide |
| 161 | 48 | $C_2H_5NH_2$ | 1-butyl-7-ethoxy-N,$\alpha,\beta,9$-tetraethyl//propionamide |
| 162 | 49 | $CH_3NH_2$ | N,1-dimethyl//butyramide |
| 163 | 49 | $(CH_3)_2NH$ | N,N,1-trimethyl//butyramide |
| 164 | 52 | n-$C_4H_9NH_2$ | N,1-dibutyl-3-ethyl-7-nitro-$\alpha,\beta,\gamma$-trimethyl//butyramide |
| 165 | 53 | $(n-C_3H_7)_2NH$ | $\alpha,\beta$-diethyl-3,3-dimethyl-N,N,1,5,9-pentapropyl//butyramide |
| 166 | 54 | n-$C_4H_9NH_2$ | N,9-dibutyl-1-ethyl-8-hydroxy-$\alpha,\alpha,\gamma,\gamma$-tetramethyl//butyramide |
| 167 | 55 | $(t-C_4H_9)_2NH$ | 5-ethoxy-1-ethyl-$\alpha,\alpha,\beta,\beta,\gamma,\gamma,3,4$-octamethyl-N,N,9-tri-t-butyl//butyramide |

TABLE IV

| EX. | NO. OF THE EXAMPLE IN WHICH STARTING MATERIAL IS PREPARED | AMINE | PRODUCT: [(PREFIX LISTED BELOW)-1,3,4,9-TETRAHYDROINDENO[2,1-c]-PYRAN-1-(SUFFIX LISTED BELOW)] PREFIX//SUFFIX |
|---|---|---|---|
| 168 | 3 | pyrrolidine | 1-[(1-methyl//propionyl]-pyrrolidine |
| 169 | 3 | piperidine | 1-[(1-methyl//propionyl]-piperidine |
| 170 | 3 | morpholine | 4-[(1-methyl//propionyl]-morpholine |
| 171 | 3 | piperazine | 1-[(1-methyl//propionyl]-piperazine |
| 172 | 3 | N-methyl-piperazine | 1-methyl-4-[(1-methyl//propionyl]piperazine |
| 173 | 3 | N-piperazine | 1-(2-hydroxyethyl)-4-[(1-methyl//propionyl]piperazine |
| 174 | 5 | pyrrolidine | 1-[(1-methyl//carbonyl]-pyrrolidine |
| 175 | 5 | morpholine | 4-[(1-methyl//carbonyl]-morpholine |
| 176 | 6 | N-ethyl-piperazine | 1-ethyl-4-[(1-ethyl-3-methyl//carbonyl]piperazine |
| 177 | 12 | piperidine | 1-[(1,4-dimethyl//acetyl]-piperidine |
| 178 | 13 | morpholine | 4-[(1-ethyl//acetyl]morpholine |
| 179 | 13 | N-piperazine-propanol | 1-(3-hydroxypropyl)-4-[(1-ethyl//acetyl]piperazine |
| 180 | 14 | pyrrolidine | 1-[(1-propyl//acetyl]pyrrolidine |
| 181 | 14 | morpholine | 4-[(1-propyl//acetyl]morpholine |
| 182 | 15 | piperidine | 1-[(1-isopropyl//acetyl]-piperidine |
| 183 | 16 | piperazine | 1-[(3-methyl-1-propyl/acetyl]-piperazine |
| 184 | 18 | N-ethyl-piperazine | 1-ethyl-4-[($\alpha$,1,9-trimethyl//acetyl]piperazine |
| 185 | 26 | pyrrolidine | 1-[(6-benzyloxy-9-isopropyl-1-methyl//acetyl]pyrrolidine |
| 186 | 27 | piperidine | 1-[(5,9-dimethyl-1-propyl//acetyl]piperidine |
| 187 | 31 | morpholine | 4-[($\alpha,\alpha$,1-triethyl-3,3-dimethyl-6-ethoxy//acetyl]-morpholine |
| 188 | 37 | piperazine | 1-[8-acetoxy-1,9-diethyl-$\alpha$,3,3-4,4-pentamethyl//propionyl]-piperazine |
| 189 | 40 | N-piperazine-ethanol | 1-(2-hydroxyethyl)-4-[(1-butyl-$\alpha,\alpha,\beta,\beta,4,6,9$-heptamethyl//propionyl]piperazine |
| 190 | 41 | pyrrolidine | 1-[(1,3,9-trimethyl-$\alpha,\alpha$-dipropyl//propionyl]pyrrolidine |
| 191 | 43 | morpholine | 4-[(1,9-diethyl-$\beta,\beta,4,4$-tetramethyl//propionyl]morpholine |
| 192 | 48 | N-propyl- | 1-propyl-4-[(1-butyl-7-ethoxy- |

TABLE IV-continued

| EX. | NO. OF THE EXAMPLE IN WHICH STARTING MATERIAL IS PREPARED | AMINE | PRODUCT: [(PREFIX LISTED BELOW)-1,3,4,9-TETRAHYDROINDENO[2,1-c]-PYRAN-1-(SUFFIX LISTED BELOW)] PREFIX//SUFFIX |
|---|---|---|---|
|  |  | piperazine | α,β,9-triethyl//propionyl]-piperazine |
| 193 | 49 | pyrrolidine | 1-[(1-methyl//butyryl]pyrrolidine |
| 194 | 49 | N-piperazine-methanol | 1-(hydroxymethyl)-4-[(1-methyl//butyryl]piperazine |
| 195 | 51 | piperidine | 1-[γ,γ-diethyl-1-propyl-3,3,9-trimethyl//butyryl]piperidine |

EXAMPLE 196

N,N-1-Trimethyl-1,3,4,9-tetrahydroindeno[2,1-c]thiopyran-1-acetamide [X; $R^1 = CH_3$, $R^2$, $R^3$, $R^4$, $R^5$, $R^6$ and $R^7 = H$, $X = S$ and $Y^1 = CH_2CON(CH_3)_2$]

1-Methyl-1,3,4,9-tetrahydroindeno[2,1-c]thiopyran-1-acetic acid (4.0 g), prepared as described in Example 4, is dissolved in anhydrous THF (60 ml). This solution is treated with triethylamine (4.7 g) at −5° C. Ethyl chloroformate (5.0 g) in THF (30 ml) is added dropwise to the solution and the resultant mixture stirred at −5° C. for 90 min. Dimethylamine (60 ml of a 40% aqueous solution) is added and stirring continued at room temperature for 30 min. The solvent is removed under reduced pressure. The remaining suspension is distributed between chloroform and water. The organic phase is separated, washed with water, dried ($MgSO_4$) and concentrated to give the title compound as a solid, nmr ($CDCl_3$) δ 1.75 (s, 3H), 2.95 (broad m, 12H), 3.50 (t, 2H), 7.26 (m, 4H).

In the same manner but replacing the 40% aqueous solution of dimethylamine with an equivalent amount of the amines of formula $HNR^8R^9$, ammonium hydroxide (concentrated), methylamine (40% aqueous solution), n-hexylamine (20% aqueous solution), diethylamine (30% aqueous solution), isopropylamine (40% aqueous solution), ethylamine (70% aqueous solution), pyrrolidine (50% aqueous solution), piperidine, morpholine, N-methylpiperazine, 1-methyl-1,3,4,9-tetrahydroindeno[2,1-c]thiopyran-1-acetamide,
N,1-dimethyl-1,3,4,9-tetrahydroindeno[2,1-c]thiopyran-1-acetamide,
N-hexyl-1-methyl-1,3,4,9-tetrahydroindeno[2,1-c]thiopyran-1-acetamide,
N,N-diethyl-1-methyl-1,3,4,9-tetrahydroindeno[2,1-c]thiopyran-1-acetamide,
1-methyl-N-isopropyl-1,3,4,9-tetrahydroindeno[2,1-c]thiopyran-1-acetamide,
N-ethyl-1-methyl-1,3,4,9-tetrahydroindeno[2,1-c]thiopyran-1-acetamide 1-[(1-methyl-1,3,4,9-tetrahydroindeno[2,1-c]thiopyran-1-yl)acetyl]-pyrrolidine,
1-[(1-methyl-1,3,4,9-tetrahydroindeno[2,1-c]thiopyran-1-yl)acetyl]-piperidine,
4-[(1-methyl-1,3,4,9-tetrahydroindeno[2,1-c]thiopyran-1-yl)acetyl]-morpholine, and
1-methyl-4-[(1-methyl-1,3,4,9-tetrahydroindeno[2,1-c]thiopyran-1-yl)acetyl]piperazine,
are obtained, respectively.

By following the procedure of Example 196 but using as starting material an equivalent amount of one of the acid compounds of formula X (X = S) described in Examples 56 to 106, instead of 1-methyl-1,3,4,9-tetrahydroindeno[2,1-c]thiopyran-1-acetic acid, and using an equivalent amount of an appropriate amine such as ammonia or a primary or secondary amine described in Example 196, then the corresponding amide compound of formula X (X = S) is obtained.

Examples of such amides are listed as products in Tables V and VI together with the appropriate starting material of formula II (X = S) and amine used for the preparation of the amide. In each case the starting material is noted by the example in which it is prepared.

TABLE V

| EX. | NO. OF THE EXAMPLE IN WHICH STARTING MATERIAL IS PREPARED | AMINE | PRODUCT: [(PREFIX LISTED BELOW)-1,3,4,9-TETRAHYDROINDENO[2,1-c]THIOPYRAN-1-(SUFFIX LISTED BELOW)] PREFIX//SUFFIX |
|---|---|---|---|
| 197 | 87 | $CH_3NH_2$ | N,1-dimethyl//propionamide |
| 198 | 87 | $NH_3$ | 1-methyl//propionamide |
| 199 | 87 | $(CH_3)_2NH$ | N,N,1-trimethyl//propionamide |
| 200 | 87 | $(C_2H_5)_2NH$ | N,N-diethyl-1-methyl//propionamide |
| 201 | 56 | $(CH_3)_2NH$ | N,N,1-trimethyl//carboxamide, nmr ($CDCl_3$) δ 1.68 (s, 3H), 2.65 (m,2H), 3.12 (s, 6H), 3.54 (m, 2H), 4.08 (m, 2H), 7.28 (m, 4H) |
| 202 | 56 | $NH_3$ | 1-methyl//carboxamide |
| 203 | 57 | $(CH_3)_2NH$ | 1-ethyl-N,N,3-trimethyl//carboxamide |
| 204 | 58 | $n-C_6H_{13}NH_2$ | 1,3-diisopropyl-6,9-dimethyl-N-hexyl//carboxamide |
| 205 | 59 | $C_2H_5NH_2$ | N-ethyl-6-hydroxy-1,3,3-trimethyl//carboxamide |
| 206 | 60 | $CH_3NH_2$ | 8,9-diethyl-N-methyl-1-propyl//carboxamide |
| 207 | 61 | $(CH_3)_2NH$ | 1-butyl-N,N-dimethyl-4,9-diisopropyl//carboxamide |
| 208 | 62 | $(CH_3)_2NH$ | 1-butyl-4,4,9-triethyl-N,N,3,3- |

TABLE V-continued

| | NO. OF THE EXAMPLE IN WHICH STARTING MATERIAL IS | | PRODUCT: [(PREFIX LISTED BELOW)-1,3,-4,9-TETRAHYDROINDENO[2,1-c]THIO-PYRAN-1-(SUFFIX LISTED BELOW)] |
|---|---|---|---|
| EX. | PREPARED | AMINE | PREFIX//SUFFIX |
| | | | tetramethyl//carboxamide |
| 209 | 63 | $CH_3NH_2$ | N,1,4-trimethyl//acetamide |
| 210 | 64 | $NH_3$ | 1-ethyl//acetamide |
| 211 | 65 | $(CH_3)_2NH$ | N,N-dimethyl-1-ethyl//acetamide |
| 212 | 64 | n-$C_6H_{13}NH_2$ | 1-ethyl-N-hexyl//acetamide |
| 213 | 64 | $(C_2H_5)_2NH$ | N,N,1-triethyl//acetamide |
| 214 | 65 | $CH_3NH_2$ | N-methyl-1-propyl//acetamide |
| 215 | 65 | $NH_3$ | 1-propyl//acetamide |
| 216 | 65 | $(CH_3)_2NH$ | N,N-dimethyl-1-propyl//acetamide |
| 217 | 65 | n-$C_6H_{13}NH_2$ | N-hexyl-1-propyl//acetamide |
| 218 | 65 | $(C_2H_5)_2NH$ | N,N-diethyl-1-propyl//acetamide |
| 219 | 66 | $CH_3NH_2$ | 1-isopropyl-N-methyl//acetamide |
| 220 | 66 | $(C_2H_5)_2NH$ | N,N-diethyl-1-isopropyl//acetamide |
| 221 | 67 | $CH_3NH_2$ | N,3-dimethyl-1-propyl//acetamide |
| 222 | 67 | $(CH_3)_2NH$ | 1-propyl-N,N,3-trimethyl//acetamide |
| 223 | 68 | $(C_2H_5)_2NH$ | 3,9-dimethyl-N,N,1,4-tetraethyl//acetamide |
| 224 | 69 | $CH_3NH_2$ | N,α,1,9-tetramethyl//acetamide |
| 225 | 69 | $NH_3$ | α,1,9-trimethyl//acetamide |
| 226 | 69 | $(CH_3)_2NH$ | N,N,α,1,9-pentamethyl//acetamide |
| 227 | 70 | $C_2H_5NH_2$ | 1-butyl-N,9-diethyl-α,α-dimethyl//acetamide |
| 228 | 71 | $CH_3NH_2$ | 1-t-butyl-N-methyl//acetamide |
| 229 | 72 | $CH_3NH_2$ | 1-butyl-N-methyl//acetamide |
| 230 | 73 | $C_2H_5NH_2$ | N,9-diethyl-8-methyl-1-propyl//acetamide |
| 231 | 74 | $(C_2H_5)_2NH$ | 6-bromo-N,N,1,9-tetraethyl//acetamide |
| 232 | 75 | $NH_3$ | 1,6-dimethyl//acetamide |
| 233 | 76 | t-$C_4H_9NH_2$ | 6-acetoxy-N,9-di-t-butyl-1-methyl//acetamide |
| 234 | 77 | $NH_3$ | 6-benzyloxy-9-isopropyl-1-methyl//acetamide |
| 235 | 78 | $(CH_3)_2NH$ | 1-propyl-N,N,5,9-tetramethyl//acetamide |
| 236 | 79 | $(C_2H_5)_2NH$ | N,N-diethyl-7-methyl-1-propyl//acetamide |
| 237 | 80 | n-$C_6H_{13}NH_2$ | 1,9-dipropyl-N-hexyl-6-nitro//acetamide |
| 238 | 81 | $CH_3NH_2$ | 1-propyl-N,4,4,9-tetramethyl//acetamide |
| 239 | 82 | $NH_3$ | 3,3-dimethyl-6-ethoxy-α,α,1-triethyl//acetamide |
| 240 | 83 | $C_2H_5NH_2$ | 1,9-dibutyl-α,α,3,3-tetramethyl-N,4,4,7-tetraethyl//acetamide |
| 241 | 84 | $CH_3NH_2$ | 1-ethyl-N,α,3,9-tetramethyl-4,4,9-tripropyl//acetamide |
| 242 | 85 | $(CH_3)_2NH_2$ | 1-propyl-N,N,α,α-tetramethyl//acetamide |
| 243 | 86 | $(C_2H_5)_2NH_2$ | 1-t-butyl-α,α-diisopropyl-N,N,3,3-4,4,5,9-oct ethyl//acetamide |
| 244 | 88 | $CH_3NH_2$ | N,9-dimethyl-5-iodo-1-isopropyl//propionamide |
| 245 | 88 | $CH_3NH_2$ | β,β-diethyl-N,9-dimethyl-7-hydroxy-1-propyl//propionamide |
| 246 | 90 | $NH_3$ | 1-butyl-3,9-dimethyl-8-nitro-β-propyl//propionamide |
| 247 | 84 | $C_2H_5NH_2$ | β,β,4,4-tetramethyl-N,1,9-triethyl//propionamide |
| 248 | 96 | n-$C_3H_7NH_2$ | α,9-dimethyl-5-methoxy-N,1,3-tripropyl//propionamide |
| 249 | 100 | $C_2H_5NH_2$ | 1-butyl-7-ethoxy-N,α,β,9-tetraethyl//propionamide |
| 250 | 101 | $CH_3NH_2$ | N,1-dimethyl//butyramide |
| 251 | 101 | $(CH_3)_2NH$ | N,N,1-trimethyl//butyramide |
| 252 | 103 | n-$C_4H_9NH_2$ | N,1-dibutyl-3-ethyl-7-nitro-α,β,γ-trimethyl//butyramide |
| 253 | 104 | (n-$C_3H_7)_2NH$ | α,β-diethyl-3,3-dimethyl-N,N,1,5,9-pentapropyl//butyramide |
| 254 | 105 | n-$C_4H_9NH_2$ | N,9-dibutyl-1-ethyl-8-hydroxy-α,α,γ,γ-tetramethyl//butyramide |
| 255 | 106 | (t-$C_4H_9)_2NH$ | 5-ethoxy-1-ethyl-α,α,β,β,γ,γ,3,4-octamethyl-N,N,9-tri-t-butyl//butyramide |

TABLE VI

| EX. | NO. OF THE EXAMPLE IN WHICH STARTING MATERIAL IS PREPARED | AMINE | PRODUCT: [(PREFIX LISTED BELOW)-1,3-4,9-TETRAHYDROINDENO[2,1-c]THIO-PYRAN-1-(SUFFIX LISTED BELOW)] PREFIX//SUFFIX |
|---|---|---|---|
| 256 | 87 | pyrrolidine | 1-[(1-methyl//propionyl]-pyrrolidine |
| 257 | 87 | piperidine | 1-[(1-methyl//propionyl]-piperidine |
| 258 | 87 | morpholine | 4-[(1-methyl//propionyl]-morpholine |
| 259 | 87 | piperazine | 1-[(1-methyl//propionyl]-piperazine |
| 260 | 87 | N-methyl-piperazine | 1-methyl-4-[(1-methyl//propionyl]piperazine |
| 261 | 87 | N-piperazine | 1-(2-hydroxyethyl)-4-[(1-methyl//propionyl]piperazine |
| 262 | 56 | pyrrolidine | 1-[(1-methyl//carbonyl]-pyrrolidine |
| 263 | 56 | morpholine | 4-[(1-methyl//carbonyl]-morpholine |
| 264 | 57 | N-ethyl-piperazine | 1-ethyl-4-[(1-ethyl-3-methyl//carbonyl]piperazine |
| 265 | 63 | piperidine | 1-[(1,4-dimethyl//acetyl]-piperidine |
| 266 | 64 | morpholine | 4-[(1-ethyl//acetyl]morpholine |
| 267 | 64 | N-piperazine-propanol | 1-(3-hydroxypropyl)-4-[(1-ethyl//acetyl]piperazine |
| 268 | 65 | pyrrolidine | 1-[(1-propyl//acetyl]pyrrolidine |
| 269 | 65 | morpholine | 4-[(1-propyl//acetyl]morpholine |
| 270 | 65 | piperidine | 1-[(1-isopropyl//acetyl]-piperidine |
| 271 | 67 | piperazine | 1-[(3-methyl-1-propyl//acetyl]-piperazine |
| 272 | 69 | N-ethyl-piperazine | 1-ethyl-4-[(α,1,9-trimethyl//acetyl]piperazine |
| 273 | 77 | pyrrolidine | 1-[(6-benzyloxy-9-isopropyl-1-methyl//acetyl]pyrrolidine |
| 274 | 78 | piperidine | 1-[(5,9-dimethyl-1-propyl//acetyl]piperidine |
| 275 | 82 | morpholine | 4-[(α,α,1-triethyl-3,3-dimethyl-6-ethoxy//acetyl]-morpholine |
| 276 | 88 | piperazine | 1-[8-acetoxy-1,9-diethyl-α,3,3-4,4-pentamethyl//propionyl]-piperazine |
| 277 | 91 | N-piperazine-ethanol | 1-(2-hydroxyethyl)-4-[(1-butyl-α,α,β,β,4,6,9-heptamethyl//propionyl]piperazine |
| 278 | 92 | pyrrolidine | 1-[(1,3,9-trimethyl-α,α-dipropyl//propionyl]pyrrolidine |
| 279 | 94 | morpholine | 4-[(1,9-diethyl-β,β,4,4-tetramethyl//propionyl]morpholine |
| 280 | 100 | N-propyl-piperazine | 1-propyl-4-[(1-butyl-7-ethoxy-α,β,9-triethyl//propionyl]-piperazine |
| 281 | 101 | pyrrolidine | 1-[(1-methyl//butyryl]pyrrolidine |
| 282 | 101 | N-piperazine-methanol | 1-(hydroxymethyl)-4-[(1-methyl//butyryl]piperazine |
| 283 | 102 | piperidine | 1-[(1-ethyl-γ,3,9-trimethyl//butyryl]piperidine |

EXAMPLE 284

N,N,1-3,4,9-tetrahydroindeno[2,1-c]pyran-1-ethylamine[1; $R^1$ = $CH_3$, $R^2$, $R^3$, $R^4$, $R^5$, $R^6$ and $R^7$ = H, X = O and Y = $CH_2CH_2N(CH_3)_2$]

The amide, N,N,1-trimethyl-1,3,4,9-tetrahydroindeno[2,1-c]pyran-1-acetamide (6.0 g), described in Example 107, in 50 ml. of dry THF is added dropwise to a stirred mixture of lithium aluminum hydride (3.0 g) in 50 ml. of ether. The reaction is stirred at room temperature for 90 min. The excess hydride is decomposed with water (24 ml). THF (100 ml.) is added and the mixture is filtered and the filtrate is dried ($MgSO_4$), filtered and the filtrate evaporated. The residue is evaporated to afford the title compound, nmr($CDCl_3$) δ 1.42 (s, 3H), 1.70–2.80 (6H), 2.22 (s, 6H), 3.30 (t, 2H), 3.97 (t, 2H), 7.30 (m, 4H).

The corresponding hydrochloric acid addition salt, N,N,1-trimethyl-1,3,4,9-tetrahydroindeno[2,1-c]pyran-1-ethylamine hydrochloride, has m.p. 266°–268° C after recrystallization from ethanol.

In the same manner but replacing lithium aluminum hydride with an equivalent amount of lithium aluminum hydride-aluminum chloride, alumimum hydride-aluminum chloride, diborane and sodium borohydride-aluminum chloride, the title compound is also obtained.

In the same manner but replacing N,N,1-trimethyl-1,3,4,9-tetrahydroindeno[2,1-c]pyran-1-acetamide with an equivalent amount of the following amides, described in Example 107, 1-methyl-1,3,4,9-tetrahydroindeno[2,1-c]pyran-1-acetamide, N,1-dimethyl-1,3,4,9-tetrahydroindeno[2,1-c]pyran-1-acetamide, N-hexyl-1-methyl-1,3,4,9-tetrahydroindeno[2,1-c]pyran-1-acetamide,
N,N-diethyl-1-methyl-1,3,4,9-tetrahydroindeno[2,1-c]pyran-1-acetamide,
1-methyl-N-isopropyl-1,3,4,9-tetrahydroindeno[2,1-c]pyran-1-acetamide,
N-ethyl-1-methyl-1,3,4,9-tetrahydroindeno[2,1-c]pyran-1-acetamide
1-[(1-methyl-1,3,4,9-tetrahydroindeno[2,1-c]pyran-1-yl)acetyl]pyrrolidine,
1-[(1-methyl-1,3,4,9-tetrahydroindeno[2,1-c]pyran-1-yl)acetyl]piperidine,
4-[(1-methyl-1,3,4,9-tetrahydroindeno[2,1-c]pyran-1-yl)acetyl]morpholine, and
1-methyl-4-[(1-methyl-1,3,4,9-tetrahydroindeno[2,1-c]pyran-1-yl)acetyl]piperazine,
there are obtained,
1-methyl-1,3,4,9-tetrahydroindeno[2,1-c]pyran-1-ethylamine,
N,1-dimethyl-1,3,4,9-tetrahydroindeno[2,1-c]pyran-1-ethylamine,
N-hexyl-1-methyl-1,3,4,9-tetrahydroindeno[2,1-c]pyran-1-ethylamine,
N,N-diethyl-1-methyl-1,3,4,9-tetrahydroindeno[2,1-c]pyran-1-ethylamine,
1-methyl-N-isopropyl-1,3,4,9-tetrahydroindeno[2,1-c]pyran-1-ethylamine,
N-ethyl-1-methyl-1,3,4,9-tetrahydroindeno[2,1-c]pyran-1-ethylamine,
1-[(1-methyl-1,3,4,9-tetrahydroindeno[2,1-c]pyran-1-yl)ethyl]pyrrolidine,
1-[(1-methyl-1,3,4,9-tetrahydroindeno[2,1-c]pyran-1-yl)ethyl]piperidine,
4-[(1-methyl-1,3,4,9-tetrahydroindeno[2,1-c]pyran-1-yl)ethyl]morpholine, and
1-methyl-4-[(1-methyl-1,3,4,9-tetrahydroindeno[2,1-c]pyran-1-yl)ethyl]piperazine, respectively.

By following the procedure of Example 284 but using as starting material an equivalent amount of one of the amide compounds of formula X described in Examples 108 to 195 instead of N,N,1-trimethyl-1,3,4,9-tetrahydroindeno[2,1-c]pyran-1-acetamide, then the corresponding compounds of formula 1 are obtained. Examples of such compounds of formula 1 are listed as products in Table VII and VIII together with the appropriate starting material. In each case the starting material is noted by the example in which it is prepared.

TABLE VII

| EXAMPLE | NO. OF EXAMPLE IN WHICH STARTING MATERIAL IS PREPARED | PRODUCT: [(PREFIX LISTED BELOW)-1,3,4,9-TETRAHYDROINDENO[2,1-c]-PYRAN-1-(SUFFIX LISTED BELOW)] |
|---|---|---|
| | | PREFIX//SUFFIX |
| 285 | 108 | N,1-dimethyl//propylamine |
| 286 | 109 | 1-methyl//propylamine |
| 287 | 110 | N,N,1-trimethyl//propylamine, nmr (CDCl$_3$) δ 1.42 (s, 3H), 3.30 (m, 2H), 3.94 (t, 2H); corresponding hydrochloric acid addition salt has m.p. 210–212° C, after recrystallization from isopropanol |
| 288 | 111 | N-ethyl-1-methyl//propylamine |
| 289 | 112 | N,N-diethyl-1-methyl//propylamine |
| 290 | 113 | N,N,1-trimethyl//methylamine, nmr (CDCl$_3$) δ 1.45 (s, 3H), 3.35 (m, 4H), 3.94 (m, 2H); corresponding hydrochloric acid addition salt has m.p. 250–251° C after recrystallization from isopropanol |
| 291 | 114 | 1-methyl//methylamine |
| 292 | 115 | 1-ethyl-N,N,3-trimethyl//methylamine |
| 293 | 116 | 1,3-diisopropyl-6,9-dimethyl-N-hexyl//methylamine |
| 294 | 117 | N-ethyl-6-hydroxy-1,3,3-trimethyl//methylamine |
| 295 | 118 | 8,9-diethyl-N-methyl-1-propyl//methylamine |
| 296 | 119 | 1-butyl-N,N-dimethyl-4,9-diisopropyl//methylamine |
| 297 | 120 | 1-butyl-4,4,9-triethyl-N,N,3,3-tetramethyl//methylamine |
| 298 | 121 | N,1,4-trimethyl//ethylamine |
| 299 | 122 | 1-ethyl//ethylamine |
| 300 | 123 | 1-ethyl-N,N-dimethyl//ethylamine |
| 301 | 124 | 1-ethyl-N-hexyl//ethylamine |
| 302 | 125 | N,N,1-triethyl//ethylamine |
| 303 | 126 | N-methyl-1-propyl//ethylamine |
| 304 | 127 | 1-propyl//ethylamine |
| 305 | 128 | N,N-dimethyl-1-propyl//ethylamine |
| 306 | 129 | N-hexyl-1-propyl//ethylamine |
| 307 | 130 | N,N-diethyl-1-propyl//ethylamine |
| 308 | 131 | 1-isopropyl-N-methyl//ethylamine |
| 309 | 132 | N,N-diethyl-1-isopropyl//ethylamine |
| 310 | 133 | 130 |
| 311 | 134 | 1-propyl-N,N,3-trimethyl//ethylamine |
| 312 | 135 | 3,9-dimethyl-N,N,1,4-tetraethyl//ethylamine |
| 313 | 136 | N,α,1,9-tetramethyl//ethylamine |
| 314 | 137 | α,1,9-trimethyl//ethylamine |
| 315 | 138 | N,N,α,1,9-pentamethyl//ethylamine |
| 316 | 139 | 1-butyl-N,9-diethyl-α,α-dimethyl//ethylamine |
| 317 | 140 | 1-t-butyl-N-methyl//ethylamine |
| 318 | 141 | 1-butyl-N-methyl//ethylamine |
| 319 | 142 | N,9-diethyl-8-methyl-1-propyl// |

TABLE VII-continued

| EXAMPLE | NO. OF EXAMPLE IN WHICH STARTING MATERIAL IS PREPARED | PRODUCT: [(PREFIX LISTED BELOW)-1,3,4,9-TETRAHYDROINDENO[2,1-c]-PYRAN-1-(SUFFIX LISTED BELOW)] |
|---|---|---|
| | | PREFIX//SUFFIX |
| 320 | 143 | 6-bromo-N,N,1,9-tetraethyl//ethylamine |
| 321 | 144 | 1,6-dimethyl//ethylamine |
| 322 | 145 | 6-acetoxy-N,9-di-t-butyl-1-methyl//ethylamine |
| 323 | 146 | 6-benzyloxy-9-isopropyl-1-methyl//ethylamine |
| 324 | 147 | 1-propyl-N,N,5,9-tetramethyl//ethylamine |
| 325 | 148 | N,N-diethyl-7-methyl-1-propyl//ethylamine |
| 326 | 149 | 1,9-dipropyl-N-hexyl-6-nitro//ethylamine |
| 327 | 150 | 1-propyl-N,4,4,9-tetramethyl//ethylamine |
| 328 | 151 | 3,3-dimethyl-6-ethoxy-α,α,1-triethyl//ethylamine |
| 329 | 152 | 1,9-dibutyl-N,4,4,7-tetraethyl-α,α,3,3-tetramethyl//ethylamine |
| 330 | 153 | 1-ethyl-N,α,3,9-tetramethyl-4,4,9-tripropyl//ethylamine |
| 331 | 154 | 1-propyl-N,N,α,α-tetramethyl//ethylamine |
| 332 | 155 | 1-t-butyl-α,α-diisopropyl-N,N,3,3-4,4,5,9-octaethyl//ethylamine |
| 333 | 156 | N,9-dimethyl-5-iodo-1-isopropyl//propylamine |
| 334 | 157 | β,β-diethyl-N,9-dimethyl-7-hydroxy-1-propyl//propylamine |
| 335 | 158 | 1-butyl-3,9-dimethyl-8-nitro-β-propyl//propylamine |
| 336 | 159 | β,β,4,4-tetramethyl-N,1,9-triethyl//propylamine |
| 337 | 160 | α,9-dimethyl-5-methoxy-N,1,3-tripropyl//propylamine |
| 338 | 161 | 1-butyl-7-ethoxy-N,α,β,9-tetraethyl//propylamine |
| 339 | 162 | N,1-dimethyl//butylamine |
| 340 | 163 | N,N,1-trimethyl//butylamine |
| 341 | 164 | N,1-dibutyl-3-ethyl-7-nitro-α,β,γ-trimethyl//butylamine |
| 342 | 165 | α,β-diethyl-3,3-dimethyl-N,N,1,5,9-pentapropyl//butylamine |
| 343 | 166 | N,9-dibutyl-1-ethyl-8-hydroxy-α,α,γ,γ-tetramethyl//butylamine |
| 344 | 167 | 5-ethoxy-1-ethyl-α,α,β,β,γ,γ,3,4-octamethyl-N,N,9-tri-t-butyl//butylamine |

TABLE VIII

| EXAMPLE | NO. OF EXAMPLE IN WHICH STARTING MATERIAL IS PREPARED | PRODUCT: [(PREFIX LISTED BELOW)-1,3,4,9-TETRAHYDROINDENO[2,1-c]-PYRAN-1-YL)-(SUFFIX LISTED BELOW)] |
|---|---|---|
| | | PREFIX//SUFFIX |
| 345 | 168 | 1-[(1-methyl//propyl]pyrrolidine |
| 346 | 169 | 1-[(1-methyl//propyl]piperidine |
| 347 | 170 | 1-[(1-methyl//propyl]morpholine |
| 348 | 171 | 1-[(1-methyl//propyl]piperazine |
| 349 | 172 | 1-methyl-4-[(1-methyl//propyl]-piperazine |
| 350 | 173 | 1-(2-hydroxyethyl)-4-[(1-methyl//propyl]piperazine |
| 351 | 174 | 1-[(1-methyl//methyl]pyrrolidine |
| 352 | 175 | 4-[(1-methyl//methyl]morpholine |
| 353 | 176 | 1-ethyl-4-[(1-ethyl-3-methyl//methyl]piperazine |
| 354 | 177 | 1-[(1,4-dimethyl//ethyl]piperidine |
| 355 | 178 | 4-[(1-ethyl//ethyl]morpholine |
| 356 | 179 | 1-(3-hydroxypropyl)-4-[(1-ethyl//-ethyl]piperazine |
| 357 | 180 | 1-[(1-propyl//ethyl]pyrrolidine |
| 358 | 181 | 4-[(1-propyl//ethyl]morpholine |
| 359 | 182 | 1-[(1-isopropyl//ethyl]piperidine |
| 360 | 183 | 1-[(3-methyl-1-propyl//ethyl]-piperazine |
| 361 | 184 | 1-ethyl-4-[(α,1,9-trimethyl//ethyl]-piperazine |
| 362 | 185 | 1-[(6-benzyloxy-9-isopropyl-1-methyl//ethyl]pyrrolidine |
| 363 | 186 | 1-[(5,9-dimethyl-1-propyl//ethyl]-piperidine |

TABLE VIII-continued

| EXAMPLE | NO. OF EXAMPLE IN WHICH STARTING MATERIAL IS PREPARED | PRODUCT: [(PREFIX LISTED BELOW)-1,3,4,9-TETRAHYDROINDENO[2,1-c]-PYRAN-1-YL)-(SUFFIX LISTED BELOW)] |
|---|---|---|
| | | PREFIX//SUFFIX |
| 364 | 187 | 4-[(α,α,1-triethyl-3,3-dimethyl-6-ethoxy//ethyl]-morpholine |
| 365 | 188 | 1-[(8-acetoxy-1,9-diethyl-α,3,3-4,4-pentamethyl//propyl]-piperazine |
| 366 | 189 | 1-(2-hydroxyethyl)-4-[(1-butyl-α,α,β,β,4,6,9-heptamethyl//propyl]piperazine |
| 367 | 190 | 1-[(1,3,9-trimethyl-α,α-dipropyl//propyl]pyrrolidine |
| 368 | 191 | 4-[(1,9-diethyl-β,β,4,4-tetramethyl//propyl]morpholine |
| 369 | 192 | 1-propyl-4-[(1-butyl-7-ethoxy-α,β,9-triethyl//propyl]piperazine |
| 370 | 193 | 1-[(1-methyl//butyl]pyrrolidine |
| 371 | 194 | 1-(hydroxymethyl)-4-[(1-methyl//-butyl]piperazine |
| 372 | 195 | 1-[γ,γ-diethyl-1-propyl-3,3,9-trimethyl//butyl]piperidine |

EXAMPLE 373

N,N,1-Trimethyl-1,3,4,9-tetrahydroindeno[2,1-c]thiopyran-1-ethylamine [1; $R^1 = CH_3$, $R^2$, $R^3$, $R^4$, $R^5$, $R^6$ and $R^7$ = H and Y = $CH_2CH_2N(CH_3)_2$]

The amide, N,N,1-trimethyl-1,3,4,9-tetrahydroindeno[2,1-c]thiopyran-1-acetamide (2.7 g), described in Example 196, in anhydrous ether (200 ml) is added dropwise to a stirred suspension of lithium alumimum hydride (1.0 g) in 100 ml of anhydrous ether. The mixture is stirred at room temperature for 30 min. Excess hydride is decomposed with water (4 ml). The mixture is filtered. The filtrate is dried ($MgSO_4$) and concentrated to give the title compound, nmr ($CDCl_3$), 1.45 (s, 3H), 3.50 (m, 2H), 7.32 (m, 4H).

The corresponding hydrochloric acid addition salt, N,N,1-trimethyl-1,3,4,9-tetrahydroindeno[2,1-c]thiopyran-1-ethylamine hydrochloride, has m.p. 265°–267° C after recrystallization from ethanol.

In the same manner but replacing lithium aluminum hydride with an equivalent amount of lithium alumimum hydride-aluminum chloride, aluminum hydride-aluminum chloride, diborane and sodium borohydride-aluminum chloride, the title compound is also obtained.

In the same manner but replacing N,N,1-trimethyl-1,3,4,9-tetrahydroindeno[2,1-c]thiopyran-1-acetamide with an equivalent amount of the appropriate amide described in Example 196, then the following corresponding indenothiopyranalkylamines are obtained:

1-methyl-1,3,4,9-tetrahydroindeno[2,1-c]thiopyran-1-ethylamine,
N,1-dimethyl-1,3,4,9-tetrahydroindeno[2,1-c]thiopyran-1-ethylamine,
N-hexyl-1-methyl-1,3,4,9-tetrahydroindeno[2,1-]thiopyran-1-ethylamine,
N,N-diethyl-1-methyl-1,3,4,9-tetrahydroindeno[2,1-c]thiopyran-1-ethylamine,
1-methyl-N-isopropyl-1,3,4,9-tetrahydroindeno[2,1-c]thiopyran-1-ethylamine,
N-ethyl-1-methyl-1,3,4,9-tetrahydroindeno[2,1-c]thiopyran-1-ethylamine,
1[(1-methyl-1,3,4,9-tetrahydroindeno[2,1-c]thiopyran-1-yl)ethyl]pyrrolidine,
1-[(1-methyl-1,3,4,9-tetrahydroindeno[2,1-c]thiopyran-1-yl)ethyl]piperidine,
4-[(1-methyl-1,3,4,9-tetrahydroindeno[2,1-c]thiopyran-1-yl)ethyl]morpholine, and
1-methyl-4-[(1-methyl-1,3,4,9-tetrahydroindeno[2,1-c]thiopyran-1-yl)-ethyl]piperazine, respectively.

By following the procedure of Example 373 but using as starting material an equivalent amount of one of the amide compounds of formula X (X = S), described in Examples 197 to 284 instead of N,N,1-trimethyl-1,3,4,9-tetrahydroindeno[2,1-c]thiopyran-1-acetamide, then the corresponding compounds of formula 1 are obtained. Examples of such compounds of formula 1 are listed as products in Table IX and X together with the appropriate starting material. In each case the starting material is noted by the example in which it is prepared.

TABLE IX

| EXAMPLE | NO. OF EXAMPLE IN WHICH STARTING MATERIAL IS PREPARED | PRODUCT: [(PREFIX LISTED BELOW)-1,3,4,9-TETRAHYDROINDENO[2,1-c]-THIOPYRAN-1-(SUFFIX LISTED BELOW)] |
|---|---|---|
| | | PREFIX//SUFFIX |
| 374 | 197 | N,1-dimethyl//propylamine |
| 375 | 198 | 1-methyl//propylamine |
| 376 | 199 | N,N,1-trimethyl//propylamine |
| 377 | 200 | N,N-diethyl-1-methyl//propylamine |
| 378 | 201 | N,N,1-trimethyl//methylamine |
| 379 | 202 | 1-methyl//methylamine |
| 380 | 203 | 1-ethyl-N,N,3-trimethyl//methylamine |
| 381 | 204 | 1,3-diisopropyl-6,9-dimethyl-N-hexyl//methylamine |
| 382 | 205 | N-ethyl-6-hydroxy-1,3,3-trimethyl// |

TABLE IX-continued

| EXAMPLE | NO. OF EXAMPLE IN WHICH STARTING MATERIAL IS PREPARED | PRODUCT: [(PREFIX LISTED BELOW)-1,3,4,9-TETRAHYDROINDENO[2,1-c]-THIOPYRAN-1-(SUFFIX LISTED BELOW)] |
|---|---|---|
| | | PREFIX//SUFFIX |
| | | methylamine |
| 383 | 206 | 8,9-diethyl-N-methyl-1-propyl//methylamine |
| 384 | 207 | 1-butyl-N,N-dimethyl-4,9-diisopropyl//methylamine |
| 385 | 208 | 1-butyl-4,4,9-triethyl-N,N,3,3-tetramethyl//methylamine |
| 386 | 209 | N,1,4-trimethyl//ethylamine |
| 387 | 210 | 1-ethyl//ethylamine |
| 388 | 211 | N,N-dimethyl-1-ethyl//ethylamine |
| 389 | 212 | 1-ethyl-N-hexyl//ethylamine |
| 390 | 213 | N,N,1-triethyl//ethylamine |
| 391 | 214 | N-methyl-1-propyl//ethylamine |
| 392 | 215 | 1-propyl//ethylamine |
| 393 | 216 | N,N-dimethyl-1-propyl//ethylamine |
| 394 | 217 | N-hexyl-1-propyl//ethylamine |
| 395 | 218 | N,N-diethyl-1-propyl//ethylamine |
| 396 | 250 | 1-isopropyl-N-methyl//ethylamine |
| 397 | 220 | N,N-diethyl-1-isopropyl//ethylamine |
| 398 | 221 | N,3-dimethyl-1-propyl//ethylamine |
| 399 | 222 | 1-propyl-N,N,3-trimethyl//ethylamine |
| 400 | 223 | 3,9-dimethyl-N,N,1,4-tetraethyl//ethylamine |
| 401 | 224 | N,$\alpha$,1,9-tetramethyl//ethylamine |
| 402 | 225 | $\alpha$,1,9-trimethyl//ethylamine |
| 403 | 226 | N,N,$\alpha$,1,9-pentamethyl//ethylamine |
| 404 | 227 | 1-butyl-N,9-diethyl-$\alpha$,$\alpha$-dimethyl//ethylamine |
| 405 | 228 | 1-tbutyl-N-methyl//ethylamine |
| 406 | 229 | 1-butyl-N-methyl//ethylamine |
| 407 | 230 | N,9-diethyl-8-methyl-1-propyl//ethylamine |
| 408 | 231 | 6-bromo-N,N,1,9-tetraethyl//ethylamine |
| 409 | 232 | 9-butyl-6-methoxy-1-methyl//ethylamine |
| 410 | 233 | 6-acetoxy-N,9-di-t-butyl-1-methyl//ethylamine |
| 411 | 234 | 6-benzyloxy-9-isopropyl-1-methyl//ethylamine |
| 412 | 235 | 1-propyl-N,N,5,9-tetramethyl//ethylamine |
| 413 | 236 | N,N-diethyl-7-methyl-1-propyl//ethylamine |
| 414 | 237 | 1,9-dipropyl-N-hexyl-6-nitro//ethylamine |
| 415 | 238 | 1-propyl-N,4,4,9-tetramethyl//ethylamine |
| 416 | 239 | 3,3-dimethyl-6-ethoxy-$\alpha$,$\alpha$,1-triethyl//ethylamine |
| 417 | 240 | 1,9-dibutyl-N,4,4,7-tetraethyl-$\alpha$,$\alpha$,3,3-tetramethyl//ethylamine |
| 418 | 241 | 1-ethyl-N,$\alpha$,3,9-tetramethyl-4,4,9-tripropyl//ethylamine |
| 419 | 242 | 1-propyl-N,N,$\alpha$,$\alpha$-tetramethyl//ethylamine |
| 420 | 243 | 1-t-butyl-$\alpha$,$\alpha$-diisopropyl-N,N,3,3,4,4,5,9-octaethyl//ethylamine |
| 421 | 244 | N-methyl-1-propyl//propylamine |
| 422 | 245 | N,N-dimethyl-1-propyl//propylamine |
| 423 | 246 | 1-butyl-3,9-dimethyl-8-nitro-$\beta$-propyl//propylamine |
| 424 | 247 | $\beta$,$\beta$,4,4-tetramethyl-N,1,9-triethyl//propylamine |
| 425 | 248 | $\alpha$,9-dimethyl-5-methoxy-N,1,3-tripropyl//propylamine |
| 426 | 249 | 1-butyl-7-ethoxy-N,$\alpha$,$\beta$,9-tetraethyl//propylamine |
| 427 | 250 | N,1-dimethyl//butylamine |
| 428 | 251 | N,N,1-trimethyl//butylamine |
| 429 | 252 | N,1-dibutyl-3-ethyl-7-nitro-$\alpha$,$\beta$,$\gamma$-trimethyl//butylamine |
| 430 | 253 | $\alpha$,$\beta$-diethyl-3,3-dimethyl-N,N,1,5,9-pentapropyl//butylamine |
| 431 | 254 | N,9-dibutyl-1-ethyl-8-hydroxy-$\alpha$,$\alpha$,$\gamma$,$\gamma$-tetramethyl//butylamine |
| 432 | 255 | 5-ethoxy-1-ethyl-$\alpha$,$\alpha$,$\beta$,$\beta$,$\gamma$,$\gamma$,-3,4-octamethyl-N,N,9-tri-t-butyl//butylamine |

TABLE X

| EXAMPLE | NO. OF EXAMPLE IN WHICH STARTING MATERIAL IS PREPARED | PRODUCT: [(PREFIX LISTED BELOW)-1,-3,4,9-TETRAHYDROINDENO[2,1-c]THIO-PYRAN-1-YL)-(SUFFIX LISTED BELOW)] PREFIX//SUFFIX |
|---|---|---|
| 433 | 256 | 1-[(1-methyl//propyl]pyrrolidine |
| 434 | 257 | 1-[(1-methyl//propyl]piperidine |
| 435 | 258 | 4-[(1-methyl//propyl]morpholine |
| 436 | 259 | 1-[(1-methyl//propyl]piperazine |
| 437 | 260 | 1-methyl-4-[(1-methyl//propyl]-piperazine |
| 438 | 261 | 1-(2-hydroxyethyl)-4-[(1-methyl//propyl]piperazine |
| 439 | 262 | 1-[(1-methyl//methyl]-pyrrolidine |
| 440 | 263 | 4-[(1-methyl//methyl]morpholine |
| 441 | 264 | 1-ethyl-4-[(1-ethyl-3-methyl//methyl]piperazine |
| 442 | 265 | 1-[(1,4-dimethyl//ethyl]-piperidine |
| 443 | 266 | 4-[(1-ethyl//ethyl]morpholine |
| 444 | 267 | 1-(3-hydroxypropyl)-4-[(1-ethyl//ethyl]piperazine |
| 445 | 268 | 1-[(1-propyl//ethyl]pyrrolidine |
| 446 | 269 | 4-[(1-propyl//ethyl]morpholine |
| 447 | 270 | 1-[(1-isopropyl//ethyl]piperidine |
| 448 | 271 | 1-[(3-methyl-1-propyl//ethyl]-piperazine |
| 449 | 272 | 1-ethyl-4-[($\alpha$,1,9-trimethyl//ethyl]piperazine |
| 450 | 273 | 1-[(6-benzyloxy-9-isopropyl-1-methyl//ethyl]pyrrolidine |
| 451 | 274 | 1-[5,9-dimethyl-1-propyl//ethyl]piperidine |
| 452 | 275 | 4{(3,3-dimethyl-6-methoxy-$\alpha,\alpha$,1-triethyl//ethyl]morpholine |
| 453 | 276 | 1-[(1-propyl//propyl]piperidine |
| 454 | 277 | 1-(2-hydroxyethyl)-4-[(1-butyl-$\alpha,\alpha,\beta,\beta$,4,6,9-heptamethyl//propyl]piperazine |
| 455 | 278 | 1-[(1,3,9-trimethyl-$\alpha,\alpha$-dipropyl//propyl]pyrrolidine |
| 456 | 279 | 4-[(1,9-diethyl-$\beta,\beta$,4,4-tetramethyl//propyl]morpholine |
| 457 | 280 | 1-propyl-4-[(1-butyl-7-ethoxy-$\alpha,\beta$,9-triethyl//propyl]-piperazine |
| 458 | 281 | 1-[(1-methyl//butyl]pyrrolidine |
| 459 | 282 | 1-(hydroxymethyl)-4-[(1-methyl//butyl]piperazine |
| 460 | 283 | 1-[1-ethyl-$\gamma$,3,9-trimethyl//butyl]piperidine |

EXAMPLE 461

N,N,1-Trimethyl-1,3,4,9-tetrahydroindeno[2,1-c]pyran-1-carboxamide [X; $R^1$ = $CH_3$, $R^2$, $R^3$, $R^4$, $R^5$, $R^6$ and $R^7$ = H, X = o and $Y^1$ = $CON(CH_3)_2$]

A mixture of indene-3-ethanol (500 mg) N,N-dimethylpyruvamide (580 mg), described by W. F. Gresham in U.S. Pat. No. 2,429,877, issued October 28, 1947, 1.7 g of phosphorus pentoxide, 0.5 g of diatomaceous earth (Celite) in 75 ml of benzene is stirred at room temperature for 15 min. and then at 70° C for 1½ hr. The reaction mixture is filtered. The filtrate is washed with water, dried ($MgSO_4$) and concentrated to give the title compound, identical to the product of Example 113.

In the same manner but using an equivalent amount of the appropriate starting material of formula II in place of indene-3-ethanol together with the appropriate $\alpha$-, $\beta$-, $\nu$- or $\delta$-ketoamide, the products listed in tables III, IV, V and VI and Examples 107 and 284 are obtained. For example, by using 5-methylindene-3-ethanol, described by J. A. Elvidge and R. G. Foster, J. Chem. Soc., 590 (1963), and the $\beta$-ketoamide, acetoacetamide in the procedure of this example, 1,6-dimethyl-1,3,4,9-tetrahydroindeno[2,1-c]pyran-1-acetamide, identical to the product of Example 144, is obtained.

EXAMPLE 462

1-Methyl-1,3,4,9-tetrahydroindeno[2,1-c]pyran-1-methanol (X; $R^1$ = $CH_3$, $R^2$, $R^3$, $R^4$, $R^5$, $R^6$ and $R^7$ = H, X = O, and $Y^1$ = $CH_2OH$)

Procedure A:

The acid intermediate of formula X, 1-methyl-1,3,4,9-tetrahydroindeno[2,1-c]pyran-1-carboxylic acid (10.4 g), described in Example 5, in 100 ml of THF is slowly added to a stirred mixture of lithium aluminum-hydride (2 g.) in 100 ml of THF. The reaction is kept at 0° C. using an ice-water bath. After addition of the acid, the excess of the hydride is destroyed with water and the precipitate is collected on a filter pad. The filtrate is evaporated. The residue is taken into ether and the ether phase is washed with water, dried ($Na_2SO_4$) and evaporated at reduced pressure to afford an oil. Chromatography of the oil on silica gel using chloroform gives the title compound, $\nu_{max}^{CHCl_3}$ 3580, 3440, 1470, 1120, 1095, 1075, 1050 $cm^{-1}$, nmr ($CDCl_3$) 1.32 (s, 3H), 2.02 (broad, 1H), 2.49 (m, 2H), 3.26 (t, 2H), 3.62 (s, 2H), 3.95 (t, 2H), 7.21 (m 4H).

Procedure B:

Alternatively, the title compound is also obtained by following the procedure of Example 2 but replacing methyl acetoacetate with an equivalent amount of the keto-alcohol lower alkyl ester, acetoxyacetone. Note that the procedure of said example includes hydrolysis of the intermediate ester.

EXAMPLE 463

N,N-1-Trimethyl-1,3,4,9-tetrahydroindeno[2,1-c]pyran-1-methylamine [1; $R^1 = CH_3$, $R^2$, $R^3$, $R^4$, $R^5$, $R^6$ and $R^7 = H$, $X = O$ and $Y = CH_2N(CH_3)_2$]

1-Methyl-1,3,4,9-tetrahydroindeno[2,1-c]pyran-1-methanol (9.0 g), described in Example 462, is dissolved in dry pyridine (20 ml.). p-Toluenesulfonyl chloride (7.4 g) is added portionwise to the vigorously stirred and cooled solution. The mixture is stirred further at 0° C for 1 hr., ice and water is then added and the aqueous mixture is extracted with ether. The combined ether extracts are washed with 10% ice-cold hydrochloric acid, water, 5% sodium bicarbonate water and dried ($Na_2SO_4$). Concentration of the extracts affords 1-methyl-1,3,4,9-tetrahydroindeno[2,1-c]pyran-1-methyl tosylate.

The latter tosylate (11.7 g) is dissolved in dry acetone (100 ml) and the resulting solution treated with sodium iodide (15 g). The mixture is stirred at room temperature for 24 hr. Most of the acetone is removed at reduced pressure, water and ice are added and the resulting brown-colored solution is extracted with ether. The combined ether extracts are washed with 10% sodium thiosulfate solution, water and dried ($Na_2SO_4$). The solvent is evaporated under reduced pressure to give a yellow oil. The oil is subjected to chromatography on silica gel and eluted with benzene. Concentration of the eluate affords 1-(iodomethyl)-1-methyl-1,3,4,9-tetrahydroindeno[2,1-c]pyran.

A mixture of the latter compound (11.7 g) in 100 ml THF and 40% aqueous dimethylamine (199 ml) is stirred at room temperature for 6 hr. Most of the tetrahydrofuran is removed at reduced pressure, the milky water solution is extracted with ether and washed with water until the water tests neutral. The extract is dried ($Na_2SO_4$) and evaporated to yield the title compound, identical to the product of Example 290.

By following the procedure of Examples 462 and 463 in sequence but using as starting material in Example 462 an equivalent amount of the appropriate ester intermediate of formula X (in the case of Procedure A) or an appropriate starting material of formula II and appropriate ketoalcohol lower alkyl ester of formula IX, described above, (in the case of Procedure B); followed by the use of an appropriate amine of formula $HNR^8R^9$, for example the amines described in Example 107, in the procedure of Example 463, then the respective compounds of formula I, for example those described in Examples 284 to 460, are obtained.

For example, in the same manner but replacing 1-methyl-1,3,4,9-tetrahydroindeno[2,1]pyran-1-methanol with 1-methyl-1,3,4,9-tetrahydroindeno[2,1-c]pyran-1-ethanol, prepared by reduction (LiAlH$_4$) of 1-methyl-1,3,4,9-tetrahydroindeno[2,1-c]pyran-1-acetic acid, there is obtained 1-methyl-1,3,4,9-tetrahydroindeno[2,1-c]pyran-1-ethyl tosylate, m.p. 86°–88° C; the latter tosylate can be treated with various amines to give the corresponding compounds of formula 1 in which $R^1$ is methyl, $R^2$ to $R^7$ are hydrogen, X is oxy, and Y is —Alk—$NR^8R^9$ wherein Alk is $CH_2CH_2$ and $R^8$ and $R^9$ are as defined herein.

EXAMPLE 464

N,1-Dimethyl-1,3,4,9-tetrahydroindeno[2,1-c]pyran-1-propylamine [1; $R^1 = CH_3$, $R^2$, $R^3$, $R^4$, $R^5$, $R^6$ and $R^7 = H$, $X = O$ and $Y = CH_2CH_2CH_2NH(CH_3)$]

A solution of triethyloxonium fluoroborate (3.5 g) and the amide of formula X, N,1-dimethyl-1,3,4,9-tetrahydroindeno[2,1-c]pyran-1-propionamide (5.5 g), described in Example 108, in 100 ml of methylene chloride is evaporated at reduced pressure and the residue dissolved in 50 ml of absolute ethanol. Sodium borohydride (1.35 g) is added in portions to the stirred solution at 0° C. When the addition is complete, stirring is continued for 18 hr. at 25° C. The solution is poured into 250 ml of water and extracted with 3 × 30 ml portions of ether. The combined extracts are washed with water, dried (MgSO$_4$) and evaporated yielding the title compound, identical to the product of Example 285.

Similarly other amides of formula X, for example those described in Examples 107 to 283, may be reduced to their corresponding indenopyran- or indenothiopyranalkylamines of formula 1.

EXAMPLE 465

1-Methyl-1,3,4,9-tetrahydroindeno[2,1-c]pyran-1-carboxaldehyde

N,N-Dicyclohexylcarbodiimide (2.87 g) is added to a cooled, stirred solution of the primary alcohol, 1-methyl-1,3,4,9-tetrahydroindeno[2,1-c]pyran-1-methanol (1.09 g), described in Example 462, in 10 ml of dimethyl sulfoxide-benzene (2:1) containing trifluoroacetic acid (0.18 ml) and pyridine (0.38 ml). The reaction is stirred at room temperature under nitrogen for 5 hr. The reaction mixture is now diluted with 100 ml of ether, followed by the dropwise addition of a solution of oxalic acid (1.26 g) in 6 ml of methanol. After thirty minutes, water (100 ml) is added and the insoluble material is collected. The organic phase is washed with water (2X), 5% aqueous sodium bicarbonate (2X) and water (2X). After drying (MgSO$_4$) the organic phase is evaporated to yield an oil. The oil is purified by chromatography on silica gel. Elution with 10% ether in benzene affords the title compound as an oil $\nu_{max}^{CHCl_3}$ 1720 cm$^{-1}$.

EXAMPLE 466

N,N-1-Trimethyl-1,3,4,9-tetrahydroindeno[2,1-c]pyran-1-methylamine [1; $R^1 = CH_3$, $R^2$, $R^3$, $R^4$, $R^5$, $R^6$ and $R^7 = H$, $X = O$ and $Y = CH_2N(CH_3)_2$]

The product of Example 465 is treated with dimethylamine and perchloric acid according to the method of N. J. Leonard and J. V. Paukstelis, J. Org. Chem., 28, 3021 (1963), to yield the corresponding immonium salt. Reduction of the latter compound with sodium borohydride according to the procedure described by E. Schenker, Angew, Chem., 73, 81 (1961), affords the title compound, identical to the product of Example 290.

By following the procedure of Examples 462, 465 and 466 in sequence but using as starting material in Example 462 an equivalent amount of the appropriate acid intermediate of formula X (in the case of Procedure A) or an appropriate starting material of formula II and the appropriate ketoalcohol lower alkyl ester of formula IX, described above, (in the case of Procedure B), followed by the use of an appropriate amine of formula $HNR^8R^9$, for example the amines described in Example 107, in the procedure of Example 465, then the respective compounds of formula I, for example those described in Examples 284 to 460, are obtained.

EXAMPLE 467

Oxidation of 1-methyl-1,3,4,9-tetrahydroindeno[2,1-c]pyran-1-carboxaldehyde, described in Example 465, with silver oxide according to the method of Delepine and Bonnet, cited above, affords 1-methyl-1,3,4,9-tetrahydroindeno[2,1-c]pyran-1-carboxylic acid, identical to the product of Example 5.

By following the procedure of Examples 462, 465 and 467, in sequence, but using as starting material in Example 462 an equivalent amount of the appropriate acid intermediate of formula IX (in the case of Procedure A) or an appropriate starting material of formula II and appropriate ketoalcohol lower alkyl ester of formula IX, described above, (in the case of Procedure B); then the respective acid compounds of formula X in which $Y^1$ is COOH or $Alk^1$COOH wherein $Alk^1$ is as defined in the first instance, for example the products of Examples 6 to 106, are obtained.

EXAMPLE 468

1-Methyl-1,3,4,9-tetrahydroindeno[2,1-c]pyran-1-methylamine [1; $R^1 = CH_3$, $R^2$, $R^3$, $R^4$, $R^5$, $R^6$ and $R^7 = H$, X = O and Y = $CH_2NH_2$]

A solution of the aldehyde, 1-methyl-1,3,4,9-tetrahydroindeno[2,1-c]pyran-1-carboxaldehyde (1.0 g), described in Example 465, aqueous hydroxylamine hydrochloride (5 ml of 5N) and aqueous sodium acetate (5.0 ml of 5N) and methanol (10 ml) is heated at 50°-60° C for 5 min. and then kept at 4° C for 16 hr. The precipitate is collected and recrystallized from ethanol-water to afford the corresponding oxime of the above aldehyde.

The latter compound (230 mg) in dry THF (10 ml) is added dropwise to a stirred mixture of lithium aluminum hydride (200 mg) in 15 ml of THF at ice bath temperature. The mixture is stirred for 1 hr., during which time it is allowed to come to room temperature. Excess lithium aluminum hydride is destroyed by the careful addition of $H_2O$/THF (1:1). Insoluble material is collected on a filter and filtrate is concentrated. The concentrate is taken up in ether. The ether solution is dried ($MgSO_4$), filtered and concentrated to afford the title compound, identical with the product of Example 291.

By following the procedures of Examples 462, 465 and 468, in sequence, but using as starting material in Example 462 an equivalent amount of the appropriate acid intermediate of formula X (in the case of Procedure A) or an appropriate starting material of formula II together with an appropriate ketoalcohol lower alkyl ester of formula IX, described above, then the respective primary amine of formula I is obtained. More specifically exemplified, by replacing 1-methyl-1,3,4,9-tetrahydroindeno[2,1-c]pyran-1-carboxylic acid with an equivalent amount of 3,3-dimethyl-6-ethoxy-$\alpha,\alpha$-triethyl-1,3,4,9-tetrahydroindeno[2,1-c]pyran-1-acetic acid, described in Example 31, in the procedure of Example 462 and subjecting the product thereof to the procedures of Example 465 and 468, then 3,3-dimethyl-6-ethoxy-$\alpha$, $\alpha,1$-triethyl-1,3,4,9-tetrahydroindeno[2,1-c]pyran-1-ethylamine, identical to the product of Example 328, is obtained.

EXAMPLE 469

1-(Iodomethyl)-1-methyl-1,3,4,9-tetrahydroindeno[2,1-c]pyran (X; $R^1 = CH_3$, $R^2$, $R^3$, $R^4$, $R^5$, $R^6$ and $R^7 = H$, X = O and $Y^1 = CH_2I$)

To a solution of indene-3-ethanol (15 g) in 150 ml of benzene, iodoacetone (12 g) is added. The mixture is heated at reflux with 5 ml of boron trifluoride-etherate and hydrated alkali-aluminum silicate (Molecular Sieves No. 4). After a total of 2 hours the reaction is cooled, filtered and washed with 5% sodium bicarbonate, water and dried over sodium sulfate. Evaporation under reduced pressure affords an oil. This oil is purified by chromatography on silica gel. Elution with benzene and concentration of the eluate gives the title compound, identical to the compound of the same name described in Example 463.

By following the procedure of Example 469 but using as starting materials an appropriate starting material of formula II, described above, together with an appropriate $\beta$, $\gamma$ or $\delta$-haloketone of formula IV described above, then the corresponding intermediates of formula X ($Y^1 = Alk^2$—L in which $Alk^2$ and L are as described in the first instance) are obtained.

In turn the last said intermediates of formula X is treated according to conditions described in Example 463 with an appropriate amine of formula $HNR^8R^9$ in which $R^8$ and $R^9$ are as described in the first instance to yield the corresponding compounds of formula I, for instance the products of Examples 284 to 289, and 386 to 438.

EXAMPLE 470

N-Ethyl-1-methyl-1,3,4,9-tetrahydroindeno[2,1-c]pyran-1-propylamine [1; $R^1 = CH_3$, $R^2$, $R^3$, $R^4$, $R^5$, $R^6$ and $R^7 = H$, X = O and Y = $CH_2CH_2NH(C_2H_5)$]

A mixture of indene-3-ethanol (4.2 g) and N-(4-oxopentyl(acetamide (3.7 g), described by L. P. Kuhn et al., J. Am. Chem. Soc., 89, 3858 (1967), in 300 ml of dry benzene is stirred and heated at reflux. Water is collected in a Dean-Stark trap. After removal of the water five drops of boron trifluoride-etherate is added and the mixture refluxed 30 min. using the water-separator again. After stirring at room temperature overnight the reaction mixture is evaporated to dryness. The solid residue is dissolved in chloroform and washed successively with 10% aqueous sodium bicarbonate, water, and brine. The chloroform solution is dried over magnesium sulfate, filtered, and evaporated to yield 1-[3-(acetamido)propyl]-1-methyl-1,3,4,9-tetrahydroindeno[2,1-c]pyran, $\nu_{max}^{CHCl_3}$ 1650 $cm^{-1}$.

The latter product (2.6 g) in 80 ml of dry THF is added to a suspension of lithium aluminum hydride in 200 ml of THF. The resultant slurry is stirred and heated as reflux for 2 hours, cooled and 2.4 g of lithium aluminum hydride is added. The mixture is heated at reflux for 16 hrs. The mixture is then decomposed with 22.4 ml of water added dropwise over 3 hrs. while stirring and cooling the mixture. The precipitate is separated by filtration. The filtrate is dried ($MgSO_4$). Removal of the solvent affords the title compound, identical to the product of Example 288.

By following the procedure of Example 470, but using as starting material an equivalent amount of the appropriate starting material of formula II, for example, those described in Examples 2 to 106 and using an equivalent amount of an appropriate ketoamide of formula

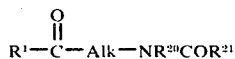

described above, then the respective secondary amine compounds of formula I are obtained.

EXAMPLE 471

1-Methyl-1-(3-nitropropyl)-1,3,4,9-tetrahydroindeno[2,1-c]pyran (X; R; = CH$_3$, R$^2$, R$^3$, R$^4$, R$^5$, R$^6$ and R$^7$ = H, X = O and Z = CH$_2$CH$_2$CH$_2$NO$_2$)

To a solution of 352 mg. of indene-3-ethanol and 273 mg. of the nitroketone, 5-nitro-2-pentanone, H. Shechter, et al., cited above, in 100 ml. of benzene is added 5 drops of boron trifluoride etherate and three drops of trifluoroacetic acid. The reaction mixture is stirred and heated at refluc under a water-separator for 18 hr. The benzene solution is cooled, washed with 10% sodium bicarbonate solution, water, saturated brine solution, and dried over magnesium sulfate. The solvent is removed and the residue is subjected to chromatography on silica gel. Elution with chloroform gives the title compound, $\nu_{max}^{CHCl_3}$ 1550 cm$^{-1}$.

Reduction of the latter compound with lithium aluminum hydride according to the procedure of Example 464 affords 1-methyl-1,3,4,9-tetrahydroindeno[2,1-c]pyran-1-propylamine, identical to the product of Example 286.

By following the procedure of Example 471 including the reduction described therein but using as starting material an equivalent amount of the appropriate starting material of formula II, for example, those described in Examples 2 to 106, and using an equivalent amount of an appropriate nitroketone of formula

described above, then the respective primary amine compounds of formula I are obtained.

EXAMPLE 472

N,N,1-Trimethyl-1,3,4,9-tetrahydroindeno[2,1-c]pyran-1-ethylamine (1; R$^1$ = CH$_3$, R$^2$, R$^3$, R$^4$, R$^5$, R$^6$ and R$^7$ = H, X = O and Z = CH$_2$CH$_2$N(CH$_3$)$_2$)

To a solution of 1-dimethylamino-3-butanone (1.0 g) dissolved in toluene (10 ml), p-toluenesulfonic acid (1.3 g) is added. The suspension is stirred for 10 min. Indene-3-ethanol (1.0 g) in toluene (5 ml) is added to the suspension and the resulting solution stirred for 2 hr. Boron trifluoride etherate (0.25 ml) is added together with ca. 0.5 g of hydrated alkali-aluminum silicate. The mixture is heated at 80° C for 30 min. The mixture is cooled and diluted with water. The organic layer is separated and the aqueous layer extracted with toluene. The organic layers are washed with water. The combined aqueous phase is rendered alkaline with conc.NH$_4$OH and extracted with toluene. The latter extract is treated with charcoal and then concentrated to afford the title compound, identical to the compound of the same name described in Example 284.

By following the procedure of Example 472 but using as starting material an equivalent amount of the appropriate starting material of formula II, for example, those described in Examples 2 to 106 and using an equivalent amount of the appropriate aminoketone of formula R$^1$CO—Alk—NR$^8$R$^9$ wherein R$^1$, Alk, R$^8$ and R$^9$ are as defined in the first instance, then the respective indenopyran- and indenochropyranalkylamines of formula I are obtained.

EXAMPLE 473

N,1-Dimethyl-1,3,4,9-tetrahydroindeno[2,1-c]pyran-1-ethylamine (1; R$^1$ = CH$_3$, R$^2$, R$^3$, R$^4$, R$^5$, R$^6$ and R$^7$ and H, X = and Y = CH$_2$CH$_2$NHCH$_3$)

A mixture of indene-3-ethanol (1.6 g), 4-(formylamino)-2-butanone (1.2 g), described by H. Bredereck, et al., Chem. Ber., 2423 (1960), benzene (40 ml) and boron-trifluoride etherate (3 ml) is stirred at reflux temperature for 3 hr. The reaction mixture is washed with saturated sodium bicarbonate solution, dried and evaporated to dryness to afford the N-formyl derivative, 1-methyl-1-[2-(formylamino)ethyl]-1,3,4,9-tetrahydroindeno[2,1-c]pyran, nmr (CDCl)$_3$ δ 3.3 (m, 4H), 6.5 (broad, 1H), 7.25 (m, 4H), 8.08 (s, 1H).

The latter N-formyl derivative (5.0 g) in 50 ml of dry ether is added to a stirred suspension of lithium aluminum hydride (1.3 g) in 50 ml of the same solvent. The reaction mixture is heated at reflux for 3 hr. decomposed with 4 ml of 30% aqueous solution of sodium-potassium tartrate and filtered. The filter cake is washed with tetrahydrofuran and the filtrate dried (MgSO$_4$). Evaporation of the combined filtrate and washings affords the title compound, mass spectrum m/e: 243 (M+), 200, 185 (base peak), identical to the product of the name described in Example 284; the corresponding hydrochloric acid addition salt has m.p. 190°–192° C.

This example is a further specific example of the preparation and conversion of intermediates of formula X (Y$^1$ = AlkNR$^{20}$COR$^{21}$), see also Example 470.

In the same manner as described in Examples 2 to 473 but replacing the starting material of formula II with the corresponding starting material of formula IIa, the indenopyran- and indenothiopyranalkylamine derivatives of formula Ia having an indeno[1,2-c]pyran or an indeno[1,2-c]thiopyran nucleus, corresponding to the aforementioned indenopyran- and indenothiopyranalkylamine of formula I of Examples 2 to 473 are obtained. This latter aspect of this invention is illustrated further in the following examples.

EXAMPLE 474

Indene-2-ethanol (11a; R$^2$, R$^3$, R$^4$, R$^5$, R$^6$ and R$^7$ = H X$^1$ = OH)

A mixture of 2-indanone (13.2 g), ethyl bromoacetate (16.7 g), benzene (150 ml) and purified zinc (6.5 g) is stirred and heated at 50° C. Iodine (0.5 g) is added to catalyze the reaction. A rather vigorous reaction sets in after about 30 min. and the heating is discontinued. After the mixture ceases boiling, 4 g of fresh zinc and 10 g of ethyl bromoacetate is added, the reaction mixture is heated at reflux for 2 hr. and allowed to stand overnight at room temperature. The zinc addition-compound is decomposed by adding 200 ml of cold 10% hydrochloric acid. The aqueous layer is separated, extracted twice with benzene, all organic extracts are combined and dried (MgSO$_4$). The filtrate is concentrated and the residue distilled under reduced pressure yielding 2-hydroxyindane-2-acetic acid ethyl ester, bp. 163°–166° C/10 mm.

The latter compound (9 g) is subject to reflux with 10 ml of $POCl_3$ for 3 hr. The $POCl_3$ is removed by distillation under reduced pressure. The residue is dissolved in 200 ml of methanol and 25 ml of 25% aqueous NaOH is added. The mixture is heated at reflux for 2 hr then concentrated under reduced pressure, diluted with water and rendered acidic with conc. HCl. The mixture is now extracted with chloroform. Evaporation of the extract gives indene-2-acetic acid, m.p. 114°–115° C., described by Ahmed and Campbell, cited above.

A solution of the latter compound (300 mg), in dry ether (60 ml) is added slowly to a stirred suspension of lithium aluminium hydride (300 mg) in anhydrous ether (40 ml). The mixture is heated at reflux for 2 hr., decomposed with 1.4 ml of water and the resulting precipitate is collected. The clear filtrate is dried and evaporated. The remaining oil dissolved in chloroform, is passed through a silica gel column. The eluate is concentrated to afford indene-2-ethanol as an oil, nmr ($CDCl_3$) δ 1.82 (s, 1H), 2.74 (t, J = 6.5, 2H), 3.36 (s (broad), 2H), 3.85 (t, J = 6.5, 2H), 6.64 (m, 1H), 7.25 (m, 4H); $\nu_{max}^{CHCl_3}$ 3600, 3450, 1625, 1470 cm$^{-1}$ (both the nmr and ir are concentration dependent.) The oil is crystallized from ether-petroleum ether to afford the product as crystals, mp 47°–49° C.

EXAMPLE 475

1-Oxoindane-2-acetic acid ethyl ester

A hexane solution containing 0.41 mole of butyllithium is diluted with 1 l. of dry ether. A solution of 1-indanone (50.3 g, 0.38 mole) in 500 ml of dry ether is added dropwise at −10° C with stirring. After the addition is completed, the reaction mixture is stirred for 30 min. A solution of ethyl bromoacetate (63 g) in ether (100 ml) is added slowly from a dropping funnel. The reaction is stopped immediately by careful addition of saturated brine solution. The organic layer is separated and washed several times with fresh portions of the same brine solution. Removal of the ether gives a viscous product which is subjected to chromatography on silica gel using hexane and hexane-benzene (1:1) as eluting solvents. A homogeneous fraction is identified by spectral features. The title compound is more polar than 1-indanone on tlc plate (silica-chloroform), Rf values being 0.65 and 0.55 respectively, $\nu_{max}^{CHCl_3}$ broad peaks at 1765 and 1725 cm$^{-1}$, 1640, 1615, 1505 and 1495 cm$^{-1}$.

The keto-ester deteriorates with time and should be used within 24 hr. Distillation of the product is not recommended.

EXAMPLE 476

1-Hydroxyindane-2-ethanol

A solution of 1-oxoindane-2-acetic acid ethyl ester acid (5 g), described in Example 475, in dry THF (20 ml) is added to a stirred slurry of lithium aluminum hydride (3.6 g) in 120 ml of the same solvent. The reaction mixture is heated at reflux for 36 hr., allowed to cool, and decomposed with 30% aqueous solution of sodium potassium tartrate (14.4 ml). After filtration, the precipitate is washed with THF. The filtrate and washing are dried. Removal of solvent gives an oil which crystallizes from benzene to give the title compound m.p. 80°–82° C.

The latter product (1.1 g), ethanol (10 ml) and concentrated sulfuric acid (4 ml) is heated at 60° C for 4 hr. After cooling, the reaction mixture is poured into ice water and extracted with ether. The extracts are washed with water, dried ($MgSO_4$) and filtered. The ether is removed by distillation and the residue is subjected to chromatography on silica gel. Elution with 9:1 chloroform-methanol affords a product identical to indene-2-ethanol, described in Example 474.

EXAMPLE 477

1-Methyl-1,3,4,9-tetrahydroindeno[1,2-c]pyran-1-carboxylic acid (Xa; $R^1 = CH_3$, $R^2$, $R^3$, $R^4$, $R^5$, $R^6$ and $R^7 =$ H, X = O and $Y^1 =$ COOH)

Indene-2-ethanol (3.5 g) described in Examples 474 and 476, is treated with ethyl pyruvate (4 g) and boron trifluoride-etherate (2 ml) in benzene (50 ml) according to the procedure of Example 2 to yield the title compound, m.p. 171°–173° C., $\nu_{max}^{nujol}$ 1720 cm$^{-1}$.

EXAMPLE 478

1-Methyl-1,3,4,5-tetrahydroindeno[1,2-c]pyran-1-acetic acid (Xa; $R^1 = CH_3$, $R^2$, $R^3$, $R^4$, $R^5$, $R^6$, and $R^7 =$ H, X = O and $Y^1 = CH_2COOH$)

Indene-2-ethanol (7.5 g) is treated with methyl acetoacetate (4 g) and boron trifluoride-etherate (20 ml) in benzene (300 ml) according to the procedure of Example 2 to yield the title compound, m.p. 145° – 147° C, $\nu_{max}^{CHCl_3}$ 3500, 3000, 1740, 1700 cm$^{-1}$.

EXAMPLE 479

N,N,1-Trimethyl-1,3,4,5-tetrahydroindeno[1,2-c]pyran-1-acetamide [Xa; $R^1 = CH_3$, $R^2$, $R^3$, $R^4$, $R^5$, $R^6$ and $R^7 =$ H, X = O and $Y^1 = CH_2CON(CH_3)_2$]

A solution of 1-methyl-1,3,4,5-tetrahydroindeno[1,2-c]pyran-1-acetic acid (6.5 g), described in Example 478, in THF (150 ml) is treated with 8.1 g of triethylamine at −5° C.

Ethyl chloroformate (8.7 g) in dry THF (50 ml) is added. The mixture is stirred for 2 hr. at −5° C. The mixture is now added to 150 ml of 40% aqueous dimethylamine and kept at ambient temperature for 2 hr. The mixture is extracted with chloroform. The extract is washed with water, dried ($MgSO_4$) and evaporated to yield the title compound, m.p. 112°–114° C, $\nu_{max}^{CHCl_3}$ 1615 cm$^{-1}$.

EXAMPLE 480

N,N,1-Trimethyl-1,3,4,5-tetrahydroindeno[1,2-c]pyran-1-ethylamine[Ia; R′=$CH_3$—, $R^2$, $R^3$, $R^4$, $R^5$, $R^6$ and $R^7 =$ H, X=O and Y=$CH_2CH_2N(CH_3)_2$]

A stirred mixture of indene-2-ethanol (2.3 g), 1-dimethylamino-3-butanone (2 g), boron trifluoride-etherate (10 ml) and toluene (10 ml) is heated at 90° C for 3 hr.

After cooling, the mixture is diluted with some toluene and rendered basic with 20% aqueous sodium hydroxide. The organic layer is separated and washed with cold 10% sulfuric acid. This acidic solution is rendered basic with 20% sodium hydroxide and extracted with toluene. The toluene is washed with water, dried ($MgSO_4$), filtered and evaporated under reduced pressure. The residue is purified by chromatography on a column of silica gel using 20 : 1 chloroform-methanol mixture as eluent. Concentration of the eluate affords the title compound, nmr ($CDCl_3$) 1.52 (s, 3H), 2.15 (s, 6H), 1.95–2.65 (m, 6H), 3.30 (s, 2H), 3.93 (t, J=5.5, 2H), 7.1–7.6 (m, 4H).

The corresponding hydrochloric acid addition salt of the title has mp. 215°–217° C after recrystallization from ethanol.

The title compound is obtained also by reduction of N,N,1-trimethyl-1,3,4,5-tetrahydroindeno [1,2-c]pyran-1-acetamide, described in Example 479 with lithium aluminium according to the procedure described in Example 284. Also obtained in this latter reaction is N,N-dimethyl-3-[2-(hydroxyethyl)indene-1-yl]butylamine, nmr (CDCl$_3$) δ 1.24 (d, J=7,3H), m/e 259M+.

In the same manner but replacing indene-2-ethanol with indene-2-ethanethiol, N,N,1-trimethyl-1,3,4,5-tetrahydroindeno[1,2-c]thiopyran-1-ethylamine, nmr (CDCl$_3$) 1.5 (s, 3H), 2.2 (s, 6H), 3.30 (s,2H), 7.2–7.6 (m,4H), is obtained.

EXAMPLE 481

Resolution of N,N,1-trimethyl-1,3,4,9-tetrahydroindeno[2,1-c]pyran-1-ethylamine

A: (−)-isomer

To a solution of N,N,1-trimethyl-1,3,4,9-tetrahydroindeno[2,1-c]pyran-1-ethylamine (5.3 g), obtained as a racemic mixture in Example 284, in 30 ml of ethanol is added a solution of l-tartaric acid (2.5 g) in 30 ml of the same solvent. The mixture is concentrated under reduced pressure (20° C, under nitrogen) to 40 ml, and kept at 4° C for 4 days. The crystalline material [2.9 g, [α]$_D^{25}$ = −46° (MeOH)] is collected and recrystallized three times from ethanol. After the fourth recrystallization, the optically active tartrate (700 mg, with constant values of mp and optical rotation) is obtained; mp 165°–168° C, [α]$_D^{25}$ = −86° (MeOH). This salt is suspended in 60 ml of a mixture of water-ether (1:2), (20 ml + 40 ml). The aqueous layer is rendered basic giving (−)-N,N,1-trimethyl-1,3,4,9-tetrahydroidroindeno[2,1-c]pyran-1-ethylamine; the corresponding hydrochloric acid addition salt, after recrystallization from isopropanol, has mp 269°–272° C, [α]$_D^{25}$ = −152.5° (MeOH).

B: (+)-isomer

To a solution of N,N,1-trimethyl-1,3,4,9-tetraindeno[2,1-c]pyran-1-ethylamine (12.0 g), obtained as a racemic mixture in Example 284, in 50 ml of ethanol is added a solution of d-tartaric acid (6g) in 50 ml of the same solvent. The mixture is concentrated under reduced pressure (20° C, under nitrogen) to 70 ml, and kept at 4° C for 3 days. The crystals [2.5 g, [α]$_D^{25}$ = +54° (MeOH)] are collected and recrystallized from 20 ml of ethanol; the optically active tartrate [1.4 g, mp 162°–165° C, [α]$_D^{25}$ = +80 (MeOH)] is collected after 48 hr. Further crystallization had no effect on the value of optical rotation. This material is suspended into a mixture water-ether (30 ml + 40 ml). The aqueous layer is rendered basic giving (+)-N,N,1-trimethyl-1,3,4,9-tetrahydroindeno[2,1-c]pyran-1-ethylamine; the corresponding hydrochloric acid addition salt, after recrystallization from isopropanol, has mp 266°–268° C; [α]$_D^{25}$ = + 152.7 (MeOH).

We claim:

1. A method of relieving the symptoms of depression in warm-blooded mammals which comprises administering to said mammal an effective amount of a compound of formula

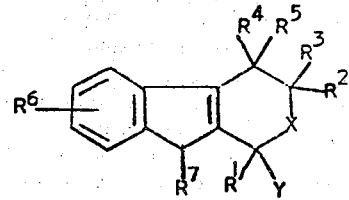

I. or

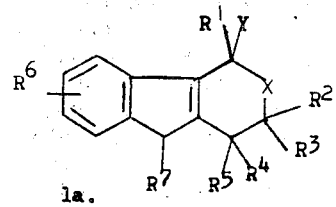

Ia.

in which $R^1$ is lower alkyl; $R^2$, $R^3$, $R^4$ and $R^5$ are the same or different selected from the group consisting of hydrogen and lower alkyl; $R^6$ is hydrogen, lower alkyl, hydroxy, lower alkoxy, lower alkanoyloxy or halo; $R^7$ is hydrogen or lower alkyl; X is oxy or thio; and Y is an amino-(lower)alkyl radical of formula —Alk—NR$^8$R$^9$ wherein Alk is an alkylene selected from the group consisting of $CR^{10}R^{11}$, $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ wherein $R^{10}$, $R^{11}$, $R^{12}$, $R^{13}$, $R^{14}$, $R^{15}$, $R^{16}$ and $R^{17}$ are hydrogen or lower alkyl and $R^8$ and $R^9$ are either the same or different selected from the group consisting of hydrogen and lower alkyl, or $R^8$ and $R^9$ together with the nitrogen atom to which they are joined form a heterocyclic amine radical selected from the group consisting of 1-pyrrolidinyl, piperidino, morpholino, piperazino, 4-(lower alkyl)-1-piperazinyl and 4[hydroxy-(lower)alkyl]-piperazinyl, and the acid additions salts thereof with pharmaceutically acceptable acids.

2. The method of claim 1 in which the compound is N,N,1-trimethyl-1,3,4,9-tetrahydroindeno[2,1-c]pyran-1-ethylamine.

3. The method of claim 1 in which the compound is N,N,1-trimethyl-1,3,4,9-tetrahydroindeno[2,1-c]pyran-1-ethylamine hydrochloride.

4. The method of claim 1 in which the compound is N,N,1-trimethyl-1,3,4,9-tetrahydroindeno[2,1-c]pyran-1-propylamine.

5. The method of claim 1 in which the compound is N,N,1-trimethyl-1,3,4,9-tetrahydroindeno[2,1-c]pyran-1-propylamine hydrochloride.

6. The method of claim 1 in which the compound is N,N,1-trimethyl-1,3,4,9-tetrahydroindeno[2,1-c]pyran-1-methylamine.

7. The method of claim 1 in which the compound is N,N,1-trimethyl-1,3,4,9-tetrahydroindeno[2,1-c]pyran-1-methylamine hydrochloride.

8. The method of claim 1 in which the compound is N,N,1-trimethyl-1,3,4,9-tetrahydroindeno[2,1-c]thiopyran-1-ethylamine.

9. The method of claim 1 in which the compound is N,N,1-trimethyl-1,3,4,9-tetrahydroindeno[2,1-c]thiopyran-1-ethylamine hydrochloride.

10. The method of claim 1 in which the compound is N,1-dimethyl-1,3,4,9-tetrahydroindeno[2,1-c]pyran-1-ethylamine.

11. The method of claim 1 in which the compound is N,N,1-trimethyl-1,3,4,5-tetrahydroindeno[1,2-c]pyran-1-ethylamine.

12. The method of claim 1 in which the compound is N,N,1-trimethyl-1,3,4,5-tetrahydroindeno[1,2-c]pyran-1-ethylamine hydrochloride.

13. The method of claim 1 in which the compound is N,N,1-trimethyl-1,3,4,5-tetrahydroindeno[1,2-c]thiopyran-1-ethylamine.

14. A pharmaceutical formulation for relieving the symptoms of depression comprising an effective amount of a compound selected from those of formula

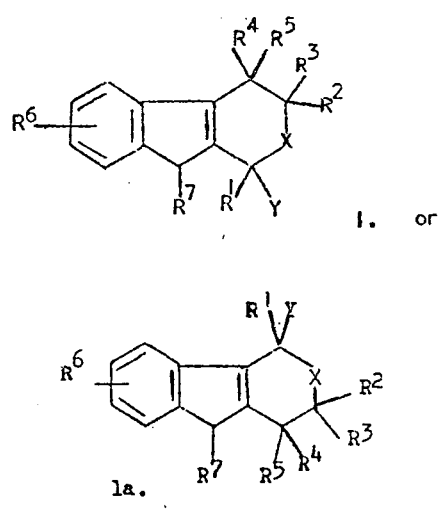

in which $R^1$ is lower alkyl; $R^2$, $R^3$, $R^4$ and $R^5$ are the same or different selected from the group consisting of hydrogen and lower alkyl; $R^6$ is hydrogen, lower alkyl, hydroxy, lower alkoxy, lower alkanoyloxy or halo; $R^7$ is hydrogen or lower alkyl; X is oxy or thio; and Y is an amino(lower)alkyl radical of formula —Alk—$NR^8R^9$ wherein Alk is an alkylene selected from the group consisting of $CR^{10}CR^{11}$, $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ wherein $R^{10}$, $R^{11}$, $R^{12}$, $R^{13}$, $R^{14}$, $R^{15}$, $R^{16}$, and $R^{17}$ are hydrogen or lower alkyl and $R^8$ and $R^9$ are either the same or different selected from the group consisting of hydrogen and lower alkyl, or $R^8$ and $R^9$ together with the nitrogen atom to which they are joined form a heterocyclic amine radical selected from the group consisting of 1-pyrrolidinyl, piperidino, morpholino, piperazino, 4-(lower alkyl)-1-piperazinyl and 4-[hydroxy(lower)alkyl]piperazinyl, and the acid addition salts thereof with pharmaceutically acceptable acids; together with a pharmaceutically acceptable carrier.

15. The pharmaceutical formulation of claim 14 in which the compound is N,N,1-trimethyl-1,3,4,9-tetrahydroindeno[2,1-c]pyran-1-ethylamine.

16. The pharmaceutical formulation of claim 14 in which the compound is N,N,1-trimethyl-1,3,4,9-tetrahydroindeno[2,1-c]pyran-1-ethylamine hydrochloride.

17. The pharmaceutical formulation of claim 14 in which the compound is N,N,1-trimethyl-1,3,4,9-tetrahydroindeno[2,1-c]pyran-1-propylamine.

18. The pharmaceutical formulation of claim 14 in which the compound is N,N,1-trimethyl-1,3,4,9-tetrahydroindeno[2,1-c]pyran-1-propylamine hydrochloride.

19. The pharmaceutical formulation of claim 14 in which the compound is N,N,1-trimethyl-1,3,4,9-tetrahydroindeno[2,1-c]pyran-1-methylamine.

20. The pharmaceutical formulation of claim 14 in which the compound is N,N,1-trimethyl-1,3,4,9-tetrahydroindeno[2,1-c]pyran-1-methylamine hydrochloride.

21. The pharmaceutical formulation of claim 14 in which the compound is N,N,1-trimethyl-1,3,4,9-tetrahydroindeno[2,1-c]thiopyran-1-ethylamine.

22. The pharmaceutical formulation of claim 14 in which the compound is N,N,1-trimethyl-1,3,4,9-tetrahydroindeno[2,1-c]thiopyran-1-ethylamine hydrochloride.

23. The pharmaceutical formulation of claim 14 in which the compound is N,1-dimethyl-1,3,4,9-tetrahydroindeno[2,1-c]pyran-1-ethylamine.

24. The pharmaceutical formulation of claim 14 in which the compound is N,1-dimethyl-1,3,4,9-tetrahydroindeno[2,1-c]pyran-1-ethylamine hydrochloride.

25. The pharmaceutical formulation of claim 14 in which the compound is N,N,1-trimethyl-1,3,4,5-tetrahydroindeno[1,2-c]pyran-1-ethylamine.

26. The pharmaceutical formulation of claim 14 in which the compound is N,N,1-trimethyl-1,3,4,5-tetrahydroindeno[1,2-c]pyran-1-ethylamine hydrochloride.

27. The pharmaceutical formulation of claim 14 in which the compound is N,N,1-trimethyl-1,3,4,5-tetrahyroindeno[1,2-c]thiopyran-1-ethylamine.

28. The pharmaceutical formulation of claim 14 in which the compound is (—)-N,N,1-trimethyl-1,3,4,9-tetrahydroindeno[2,1-c]pyran-1-ethylamine hydrochloride.

29. The pharmaceutical formulation of claim 14 in which the compound is (+)-N,N,1-trimethyl-1,3,4,9-tetrahydroindeno[2,1-c]pyran-1-ethylamine hydrochloride.

30. The method of claim 1 in which the compound is (—)-N,N,1-trimethyl-1,3,4,9-tetrahydro[2,1-c]pyran-1-ethylamine hydrochloride.

31. The method of claim 1 in which the compound is (+)-N,N,1-trimethyl-1,3,4,9-tetrahydro[2,1-c]pyran-1-ethylamine hydrochloride.

32. The method of claim 1 in which the compound is N,1-dimethyl-1,3,4,9-tetrahydroindeno[2,1-c]pyran-1-ethylamine hydrochloride.

* * * * *